(12) United States Patent
Wilson et al.

(10) Patent No.: US 7,045,303 B1
(45) Date of Patent: May 16, 2006

(54) SCREENING METHODS FOR COMPOUNDS USEFUL IN THE TREATMENT OF POLYCYSTIC KIDNEY DISEASE

(76) Inventors: Patricia D. Wilson, 525 E. 80th St., Apt. #8D, New York, NY (US) 10021; Christopher R. Burrow, 525 E. 80th St., Apt. #8D, New York, NY (US) 10021

( * ) Notice: Subject to any disclaimer, the term of this patent is extended or adjusted under 35 U.S.C. 154(b) by 0 days.

(21) Appl. No.: 09/478,737

(22) Filed: Jan. 6, 2000

(51) Int. Cl.
| | |
|---|---|
| G01N 33/566 | (2006.01) |
| C12N 15/00 | (2006.01) |
| C12N 15/63 | (2006.01) |
| C12N 15/12 | (2006.01) |
| C07K 14/00 | (2006.01) |

(52) U.S. Cl. .................. 435/7.2; 435/69.1; 435/320.1; 435/325; 530/350

(58) Field of Classification Search .............. 435/7.2, 435/69.1, 320.1, 225; 530/350
See application file for complete search history.

(56) References Cited

OTHER PUBLICATIONS

Van Adelsberg, J. Peptides from the PKD Repeats of Polycystin, the PKD Gene Product, Modulate Pattern Formation in the Developing Kidney. Developmental Genetics 24:299-308(1999).*
Huan, Y.-H..; Van Adelsberg, J. Peptides derived from the PKD1 repeats of polycystin inhibit kidney development in vitro by an effect on the ureteric bud. Journal of the American Society of Nephrology, (Sep., 1997) vol. 9, No. Abstr. Issue, pp 373A.*
Van Adelsberg, J. Peptides from the PKD Repeats of Polycystin, the PKD Gene Product, Modulate Pattern Formation in the Developing Kidney. Developmental Genetics 24:299-308(1999).*
Wilson et al. Co expression of the PKD-1 protein with matrix receptor and adhesion plaque proteins in human fetal and ADPKD epithelia in vitro. Molecular Biology of the Cell (1996) vol. 7, No. Suppl., pp 245A.*
Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Gabow et al., "Polycystic Kidney Disease: Prospective Analysis of Nonazotemic Patients and Family Members", 1984, *Ann. Intern. Med.*, 101:238-247.
Winson et al., "Defined Human Renal Tubular Epithelia In Culture: Growth, Characterization, And Hormonal Response", *American Physiological Society*, 1985, ppF436-F443.
Racusen et al., "Renal Proximal Tubular Epithelium From Patients With Nephropathic Cystinosis: Immortalized Cell Lines as *in vitro* Model Systems", 1995, *Kidney International*, 48:536-543.
Winson et al., "A New Method For Studying Human Polysystic Kidney Disease Epithelia In Culture", 1986, *Kidney International*, 30:371-378.
Winson et al., "Reversed polarity of Na$^+$-K$^+$- ATPase: Mislocation To Apical Plasma Membranes In Polycystic Kidney Disease Epithelia", 1991, *Am. J. Physiol.* 260:F420-F430.
Wilson, "Monolayer Cultures of Microdissected Renal Tubule Epithelial Segments", 1991, *J. Tiss. Cult. Meth.*, 13:137-142.
European PKD Consortium, "The Polycystic Kidney Disease 1 Gene Encodes a 14 kb. Transcript and Lies within a Duplicated Region on Chromosome 16", 1994, *Cell* 77:882-894.
International PKD Consortium, "Polycystic Kidney Disease: The Complete Structure of the *PKD1* Gene and Its Protein", 1995, *Cell* 81:289-298.
Hughes et al., "The Polycystic Kidney Disease 1 (*PKD1*) Gene Encodes A Novel Protein With Multiple Cell Recognition Domains", 1995, *Nat Genet* 10:151-160.
Wilson, 1996, In *Polycystic Disease*, Oxford.
Moy et al., "The Sea Urchin Sperm Receptor for Egg Jelly Is a Modular Protein with Extensive Homology to the Human Polycystic Kidney Disease Protein, PKD1", 1996, *J. Cell. Biol.* 133:809-817.
Peral et al., "Screening the 3' Region of the Polycystic Kidney Disease 1 (*PKD1*) Gene Reveals Six Novel Mutations", 1996, *Am. J. Hum. Gent.* 58:86-96.

(Continued)

*Primary Examiner*—Joseph Murphy
(74) *Attorney, Agent, or Firm*—Baker Botts LLP

(57) ABSTRACT

The present invention provides cell-based screening assays designed to identify agents that regulate the activity of the polycystic kidney disease proteins encoded by the PKD-1 and PKD-2 genes and that may be useful in the treatment of polycystic kidney disease. The assays of the invention comprise the contacting of genetically engineered cells expressing a mutant or truncated PKD gene product with a test agent and assaying for a decrease in the PKD mediated mutant phenotype. Characteristics associated with such a mutant phenotype include increased adherence to type I collagen coated surfaces; apical expression of NaK-ATPase on the cell membrane; increased expression of β-2-NaK-ATPase; and decreased focal adhesion kinase (FAK) incorporation into focal adhesion complexes, and inability to form tubular structures in a gel matrix. To facilitate the screening methods of the invention, cells may be genetically engineered to express epitope tagged PKD gene products and/or epitope tagged PKD interacting proteins (PKD-IP). Such interacting proteins include, for example, focal adhesion complex proteins such as FAK, paxillin, vinculin, talin and the like.

17 Claims, 19 Drawing Sheets

OTHER PUBLICATIONS

Figures 1A, 1B:
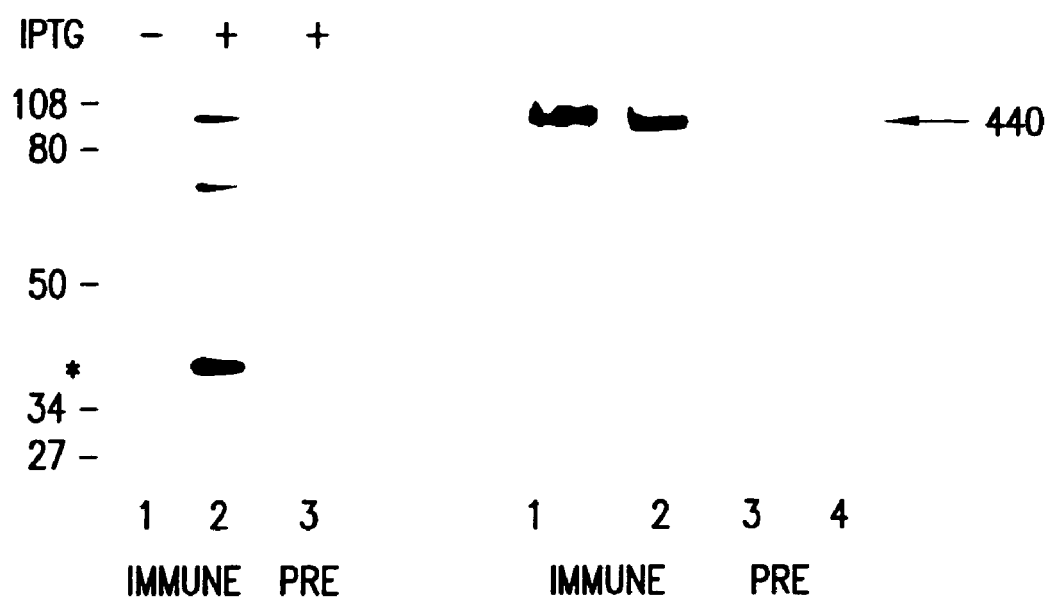
Figure 2A:
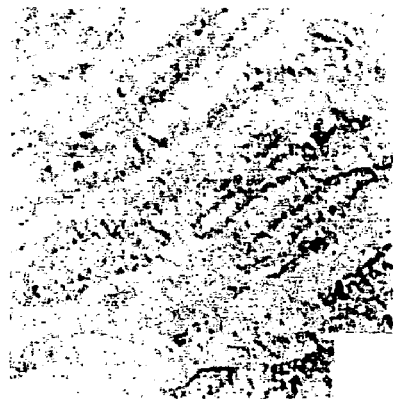
Figure 2B:
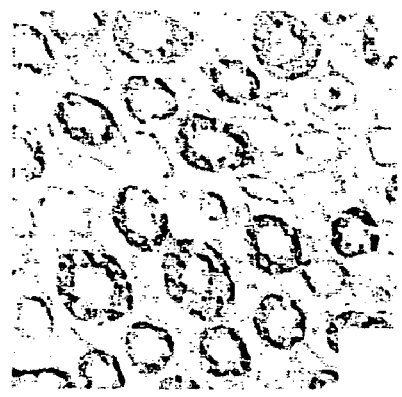
Figure 2C:
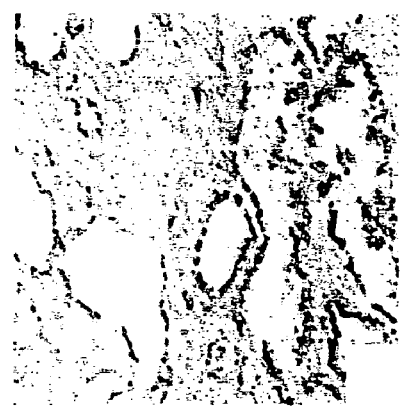
Figure 2D:
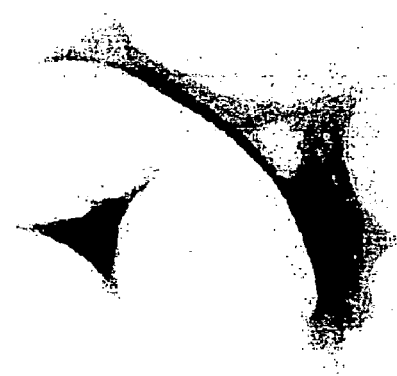
Figure 2E:
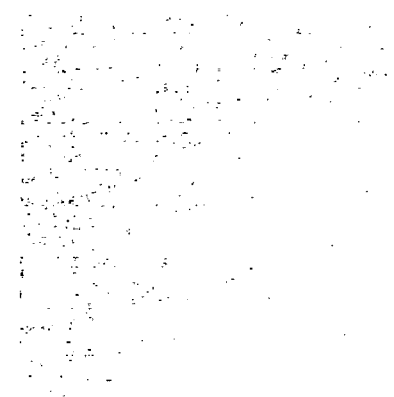
Figure 2F:
Figure 2G:
Figure 2H:
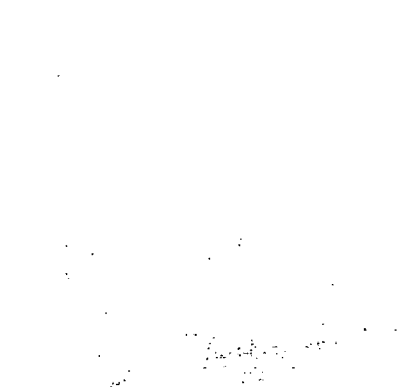

Mochizuki et al., "*PKD2,* a Gene for Polyscystic Kidney Disease That Encodes an Integral Membrance Protein", 1996, *Science* 272:1339-1342.

Tsiokas et al., "Homo- and Heterodimeric Interactions Between The Gene Products of *PKD1* and *PKD2*", 1997, *Proc. Natl. Acad. Sci.* 94:6965-6970.

Qian et al., "PKD1 Interacts With PKD2 Through A Probable Coiled-Coil Domain", 1997, *Nature Genet.* 16:179-183.

Wilson et al., 1998, *J. Cell. Biol.* vol. 9:358A.

Wilson et al., "Cystic Disease of the Kidney: Role of Adhesion Molecules in Normal and Abnormal Tubulogenesis", 1999, *Exp. Nephrol,* 7:114-124.

Wilson et al., "Pathophysiology and Clinical Management of Polycystic Kidney Diseace in Women", 1999, Seminars in Nephrology 19:123-132.

Barr et al., "A Polyscystic Kidney-Disease Gene Homologue Required For Male Mating Behaviour in *C.elegans*", 1999, *Nature,* 401:386-389.

Wilson, "In Vitro Methods in Renal Research", Section III: Research Methods: Chapter 14, pp269-281.

Wilson, "Pathogenesis of Polysystic Kidney Disease: Altered Cellular Function", Chapter 6, pp. 125-163.

Peral et al., 1995, "Splicing mutations of the polycystic kidney disease 1 gene encodes a 14kb transcript and lies within a duplicated region on chromosome 16, " Cell 77:881-894.

The European Polycystic Kidney Disease Consortium, 1994, "The polycystic kidney disease 1 gene encodes a 14kb transcript and lie within a duplicated region on chromosome 16," Cell 77:881-894.

Watnick et al., 1997, "An unusual pattern of mutation in the duplicated portion of *PKD1* is revealed by use of a novel strategy for mutation detection," Human Molecular Genetics 6:1473-1481.

Longa et al., 1997, "A Large *TSC2* and *PKD1* gene deletion is asociated with renal and extrarenal signs of autosomal dominant polycystic kidney disease," Nephrology Dialysis Transplantation 12:1900-1907.

Thomas et al., 1999, "Identification of mutations in the repeated part of the autosomal dominant polycystic kidney disease type 1 gene, PKD1, by long-range PCR," Am. J. Human Genetics 65:39-49.

\* cited by examiner

SEQUENCE LISTING

<160> NUMBER OF SEQ ID NOS: 1

<210> SEQ ID NO 1
<211> LENGTH: 31
<212> TYPE: PRT
<213> ORGANISM: "Human Sequence"

<400> SEQUENCE: 1

```
Leu Pro Ser Arg Ser Ser Arg Gly Ser Lys Val Ser Pro Asp Val Pro
 1               5                  10                  15

Pro Pro Ser Ala Gly Ser Asp Ala Ser His Pro Ser Thr Ser Ser
            20                  25                  30
```

SCREENING METHODS FOR COMPOUNDS USEFUL IN THE TREATMENT OF POLYCYSTIC KIDNEY DISEASE

1. INTRODUCTION

The present invention provides cell-based screening assays designed to identify agents that regulate the activity of the polycystic kidney disease proteins encoded by the PKD-1 and PKD-2 genes and that may be useful in the treatment of polycystic kidney disease. The assays of the invention comprise the contacting of genetically engineered cells expressing a mutant or truncated PKD gene product with a test agent and assaying for a decrease in the PKD mediated mutant phenotype. Characteristics associated with such a mutant phenotype include increased adherence to type I collagen coated surfaces; apical expression of NaK-ATPase on the cell membrane; increased expression of β-2-NaK-ATPase; and decreased focal adhesion kinase (FAK) incorporation into focal adhesion complexes, and inability to form tubular structures in a gel matrix. To facilitate the screening methods of the invention, cells may be genetically engineered to express epitope tagged PKD gene products and/or epitope tagged PKD interacting proteins (PKD-IP). Such interacting proteins include, for example, focal adhesion complex proteins such as FAK, paxillin, vinculin, talin and the like.

2. BACKGROUND OF THE INVENTION

Autosomal dominant polycystic kidney disease (ADPKD) is the most common lethal genetic disease inherited as a dominant trait in humans, with a prevalence of 1:1,000 live births. The disease afflicts approximately 6 million people world-wide, and accounts for 5–7% of all patients on dialysis in the United States (Gabow, 1984, *Ann. Intern. Med.* 101:238–247). Mutations in the PKD-1 gene account for 85% of ADPKD, while mutations in the PKD-2 gene account for 10% of the disease. In both cases, ADPKD is characterized by progressive, massive cystic enlargement of renal tubules resulting from increased proliferation, aberrant secretion, altered membrane protein polarity, and extracellular matrix abnormalities correlated with a failure to down-regulate certain fetal genes after birth (Wilson, 1996, *In Polycystic Kidney Disease, Oxford Clinical Nephrology Series*, Watson M. L. and Torres V. E. eds. p. 124–163).

Approximately 50% of patients who inherit a mutant PKD-1 gene will develop endstage renal failure, typically in the 5th decade of life, necessitating renal replacement therapy by dialysis or transplantation. Since progression is usually slow and is a consequence of gradual loss of renal function as cysts continue to enlarge and destroy intervening normal renal tubules, this presents a window of opportunity for potential drug therapies that would inhibit cyst expansion.

The PKD-1 gene maps to human chromosome 16p13.3, has 46 exons, encodes a 14.5 kb transcript with a 12,912 basepair open reading frame and translates into a 4303 amino acid ($\geq$462 kDa) protein, referred to as "polycystin-1" (European PKD Consortium, 1994, *Cell* 77:882–894; International PKD Consortium, 1995, *Cell* 81:289–298). The predicted amino acid sequence of the expressed protein suggests that the first 23 amino acids at the N-terminus act as a signal sequence, followed by two cysteine-flanked leucine rich repeats (LRR) which are strongly predictive of an extracellular location, protein—protein interactions and adhesion properties (Hughes et al., 1995, *Nat Genet* 10:151–160). Other putative extracellular domains include a C-lectin-like motif and a region with high homology to the receptor for egg jelly of sea urchins (REJ), implying potential calcium influx regulation (Moy et al., 1996, *J. Cell. Biol.* 133:809–817). The protein has several regions of high hydrophobicity and predicts 9–11 transmembrane domains and an intracellular carboxy terminal tail of 226 amino acids with putative binding sites for signal transduction molecules, including a SH2 site for tyrosine phosphorylation (YEMV) and two putative protein kinase C sites (RSSR) for serine phosphorylation.

The polycystin-1 protein is localized to areas of contact between the cell and matrix shortly after adhesion to type I collagen matrix. In addition, there is co-localization with defining focal adhesion proteins, namely α2β1-integrin, vinculin, α-actin, talin, paxillin, focal adhesion kinase ($pp125^{FAK}$) and $pp60^{c-src}$ (Wilson et al., 1998, *J Cell. Biol. Vol.* 9: 358A). Similar basally located polycystin-1-containing bodies have been demonstrated in vivo in human fetal ureteric bud epithelia in cell membrane regions in contact with type I collagen.

The overall predicted structure of the polycystin-1 protein and in vitro results with regard to matrix adhesion and phosphorylation assays, suggest that polycystin-1 functions as a matrix receptor mediating transfer of information from the extracellular matrix to the actin cytoskeleton, resulting in signal transduction that culminates in the nuclear regulation of gene transcription. This is suggested by the findings that all PKD-1 mutations mapped to date would predict the translation of a truncated protein product, lacking varying amounts of the C-terminal domain (CTD), including a potential SH2 site, and mutations that result in the failure to down regulate fetal expression of the β2 subunit of NaK-ATPase with consequent disruption of membrane polarization of NaK-ATPase (Peral et al., 1996, *Am. J. Hum. Gent.* 58:86–96). Of additional interest, ADPKD epithelia have lower levels of PKD-1 tyrosine phosphorylation and fail to recruit FAK to the basally located multi-protein bodies.

In normal mature kidneys, NaK-ATPase is comprised of α1β1 heterodimers located at the basolateral membranes of renal tubules and is associated with vectorial Na+ export into the basal cell space (blood side) driving ion gradients for fluid reabsorption. In normal fetal kidneys and also in ADPKD kidneys, the β2 subunit of NaK-ATPase heterodimerizes with α1 subunits which are "mis" targeted to apical plasma membranes, thus driving fluid secretion (Wilson et al., 1991, *Am. J. Physiol.* 260:F420 F430). The failure to repress β2 transcription in adult kidneys results, therefore, in fluid secretion and expansion of renal tubule lumens into cysts.

Less is known about the PKD-2 gene, which has been mapped to human chromosome 4q 21–23, encodes a 5.4 kb transcript and translates into a predicted 110 kDa protein, "polycystin-2" (Mochizuki et al., 1996, *Science* 272:1339–1342). Unlike polycystin-1, the PKD-2 encoded protein has intracellular C— and NH— termini, 6 transmembrane domains with a putative EF hand and coiled-coil domain in the C-terminal region and putative SH3 sites in the N-terminal region. Yeast 2 hybrid studies have suggested potential interactions of PKD-1 and PKD-2 coiled-coil domains and some co-localizations have been suggested, however, in strict contrast to polycystin-1, polycystin-2 is not developmentally regulated (Tsoikas et al., 1997, *Proc. Natl. Acad. Sci.* 94:6965–6970; Qian et al., 1997, *Nature Genet.* 16:179–183).

3. SUMMARY OF THE INVENTION

The present invention relates to cell-based screening assays designed to identify agents that regulate the activity of polycystic kidney disease proteins (encoded by the PKD-1 and PKD-2 genes). The assay system of the invention is based on the use of eukaryotic cells containing naturally occurring mutations in the PKD genes and/or eukaryotic cells genetically engineered to express different forms of the polycystic kidney disease genes (PKD genes) including wild type, mutant, truncated, or epitope tagged PKD encoded proteins. In specific nonlimiting examples of the invention, human renal cells are engineered to express mutant or truncated forms of PKD protein and express a mutant phenotype which includes one or more characteristics associated with renal epithelial cells from patients with polycystic kidney disease, for example, increased adherence to type I collagen coated surfaces; apical expression of NaK-ATPase on the cell membrane; increased expression of β-2-NaK-ATPase; and decreased FAK incorporation into focal adhesion complexes, to name a few.

The assays provided by the present invention are designed to screen for compounds or compositions that modulate PKD activity, i.e., compounds or compositions that act as agonists or antagonists of PKD, and thereby regulate PKD mediated signal transduction and extracellular matrix interactions with the plasma membrane and cell cytoskeleton. The invention also relates to assays designed to screen for compounds or compositions that modulate PKD gene expression, i.e., compounds that modulate expression of PKD, or production or activity of transcription factors involved in PKD gene expression. Agents identified using the cell-based assays of the invention may be useful in the treatment of renal cystic disease.

In addition, the assays of the invention may be used to identify and/or validate protein interactions between PKD and binding partners within the cell, identified using different model host systems, i.e., *C. elegans*. To this end, cells endogenously or genetically engineered to express PKD may be further engineered to express PKD interacting proteins. Various standard assays may be used to validate such protein interactions and/or to serve as a basis for screening assays designed to identify agents that regulate the formation of such protein complexes.

3.1 Definitions

As used herein, italicizing the name of a gene shall indicate the gene, in contrast to its encoded protein product which is indicated by the absence of italicizing. For example, PKD shall mean the PKD gene, whereas PKD shall indicate the PKD encoded protein product. Unless otherwise specified, PKD shall refer to a PKD-1 or PKD-2 gene of any species, whereas PKD shall indicate an PKD-1 or PKD-2 encoded protein products (also referred to as polycystin-1 and polycystin-2, respectively) of any species. Such PKD genes and encoded proteins include, but are not limited to, those described by Mochizuki T et al. (1996, *Science* 272:1339–1342); The International Polycystic Kidney Disease Consortium (1995, *Cell* 81:289–298); and Barr and Sternberg (1999, *Nature* 401:386–389).

4. BRIEF DESCRIPTION OF THE DRAWINGS

FIG. 1A–B. Characterization of anti-polycystin-1 antibody. Western immunoblot analysis using 1:12,500 dilution of anti-peptide (aa 4161–4191) polyclonal antiserum raised in rabbits. FIG. 1A. PKD 1-C-terminal domain (aa 4105–4303) fusion protein before (lane 1) and after (lane 2) IPTG induction. Human fusion protein is denoted by * the predicted molecular weight. Incubation with pre-immune serum did not detect bands. FIG. 1B. Human fetal collecting tubule cell lysates were incubated in immune serum (lanes 1 and 2) or pre-immune serum (lanes 3 and 4). A >440 kDa band was detected in lanes 1 and 2.

FIGS. 2A–H. Peptide competition of immunocytochemical staining with anti-polycystin-1 antibody. Panels A–D, immunohistochemistry without pre-adsorption; Panels E–H, immunohistochemistry after preadsorption with 31 amino acid polycystin-1 peptide (100 μg/ml). A and E, 16-week human fetal kidney (anti-polycystin-1 1:500); B and F, 39 year normal adult kidney medulla (anti-polycystin-1 1:500); C and G, endstage autosomal dominant polycystic kidney disease (anti-polycystin-1 1:500); D and H, cultured autosomal dominant polycystic disease epithelia (anti-polycystin-1 1:1,000).

FIGS. 3A–H. Localization of polycystin-1 in human renal tissues and epithelial cell lines. Immunocytochemical localization of polycystin-1 in human renal tissues (Panels A–D) and nephron segment-specific epithelial cell cultures (Panels E–H). A. Human fetal kidney (12 weeks gestation). Note staining in ureteric bud-derived collecting duct epithelia (arrows). X 125. B. Normal, perfused, adult human kidney: inner medullary collecting tubules show light staining. X 60. C. Cystic ADPKD kidney: intense staining in cyst lining epithelia. X 60. D. Absence of staining in ADPKD kidney incubated with pre-immune serum. X 100. E. Normal human fetal collecting tubule epithelial cell line: intense staining. X 125. F. Normal adult collecting tubule cell line: weak staining. X 60. G. ADPKD epithelial cell line: Intense staining. X 125. H. Absence of staining in ADPKD epithelial cell line incubated in preimmune serum. X 100.

Figure 4A:
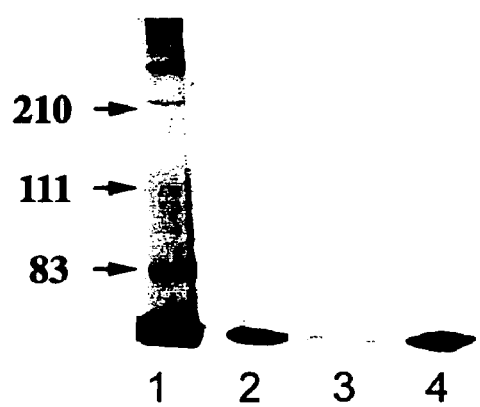
Figure 4B:
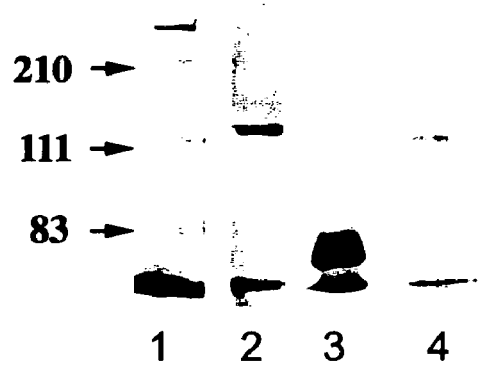
Figure 4C:
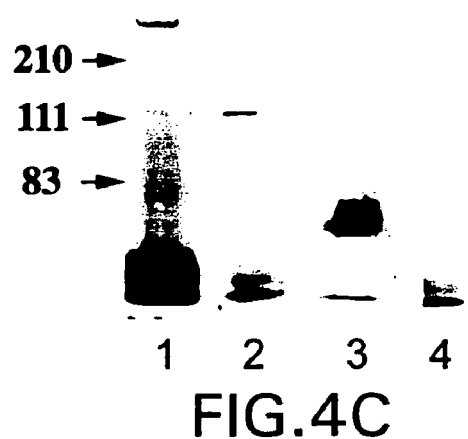

FIGS. 4A–C. Co-immunoprecipitation of polycystin-1 with focal adhesion proteins. FIG. 4A. Specificity of polycystin-1 immunoprecipitation in human fetal collecting tubule cells. Lane 1, immunoprecipitation with anti-polycystin-1 followed by Western analysis with anti-polycystin 1. Note major band at >440 kDa and minor band at 210 kda. Lane 2, immunoprecipitation control using protein A/G agarose beads omitting anti-polycystin-1 antiserum. Lane 3, control omitting anti-polycystin-1 antiserum in immunoblot. Lane 4, immunoprecipitation control using preimmune serum instead of anti-polycystin-1 antiserum. FIG. 4B. Co-immunoprecipitation with polycystin-1 in normal human fetal collecting tubule epithelia. Immunoprecipitation with anti-polycystin-1 followed by Western immunoblot with anti-polycystin-1 (Lane 1); anti-vinculin (lane 2); anti-paxillin (lane 3); anti-pp125$^{FAK}$ (lane 4). Note the presence of 130 kDa vinculin band, 68 kDa paxillin band and 125 kDa FAK band in lanes 2, 3 and 4, respectively. Equal protein loading of 20 mg per lane. C. Co-immunoprecipitation of proteins with polycystin-1 in ADPKD epithelia. Conditions as in B. Note presence of vinculin (lane 2) and paxillin (lane 3) in the co immunoprecipitates but the absence of pp125$^{FAK}$ (lane 4).

Figures 5A, 5B:
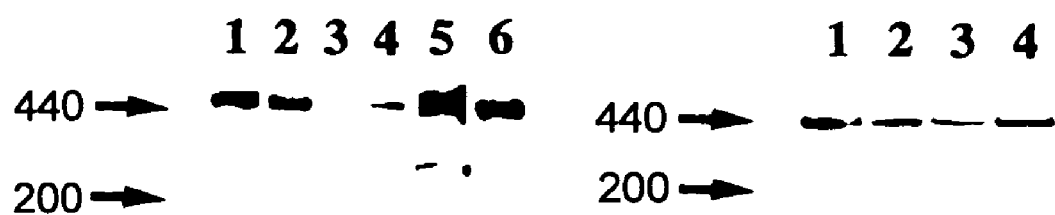

FIGS. 5A–B. Western Immunoblot analysis of polycystin-1 in human renal epithelia anti-C-terminal peptide antibody 1:12,500. FIG. 5A. Tissue extracts SDS-PAGE: Lanes 1 and 2 fetal kidneys; lanes 3 and 4 normal adult kidneys; lanes 5 and 6 ADPKD kidneys. Equal protein loading 20 mg per lane. FIG. 5B. Cultured epithelial cell extracts, SDS-PAGE: Lanes 1 primary culture of human fetal collecting tubule epithelia (HFCT); lane 2 immortalized HFCT clonal cell line; lane 3, primary culture of ADPKD epithelia; lane 4, immortalized ADPKD clonal cell line. Equal protein loading 20 mg per lane. Note band of >440 kDa ferritin marker position, consistent with the predicted molecular weight of the full length polycystin-1 protein. Additional band at 210 kDa was sometimes also detected.

Figure 6A:
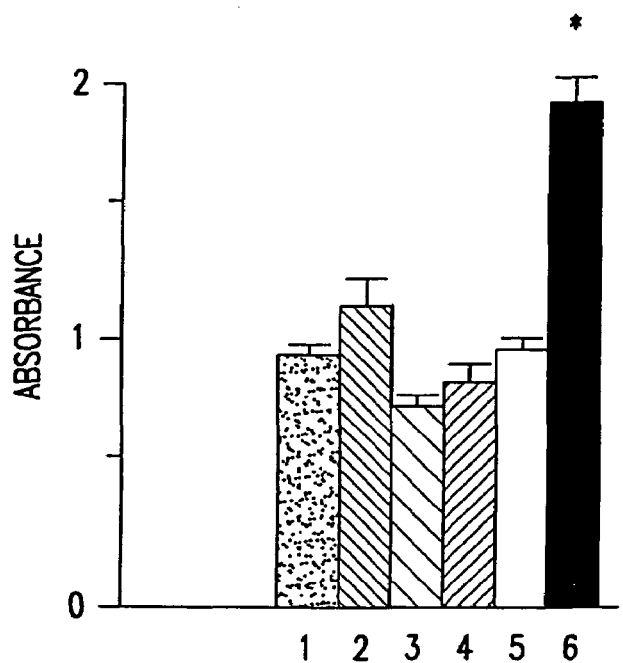
Figure 6B:
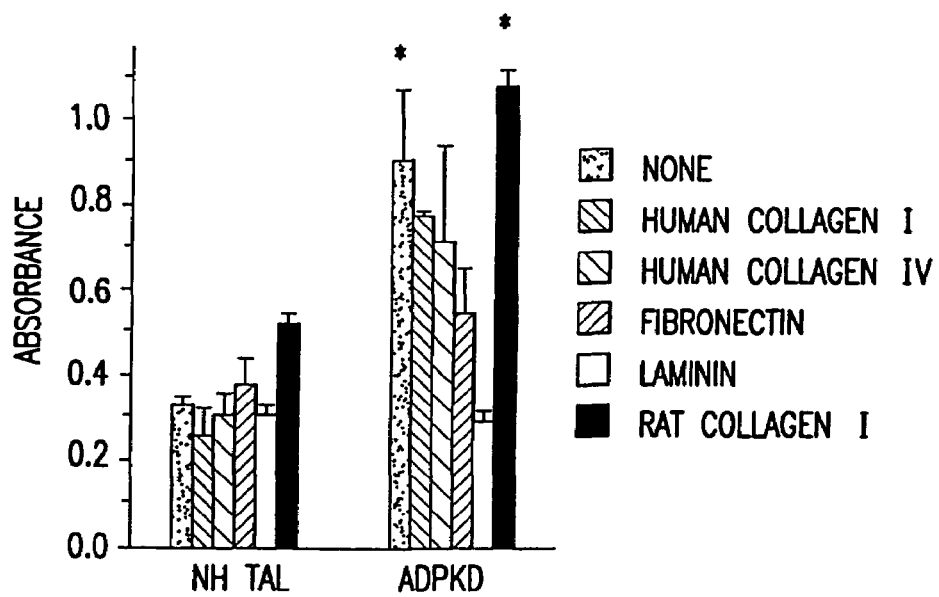
Figure 6C:
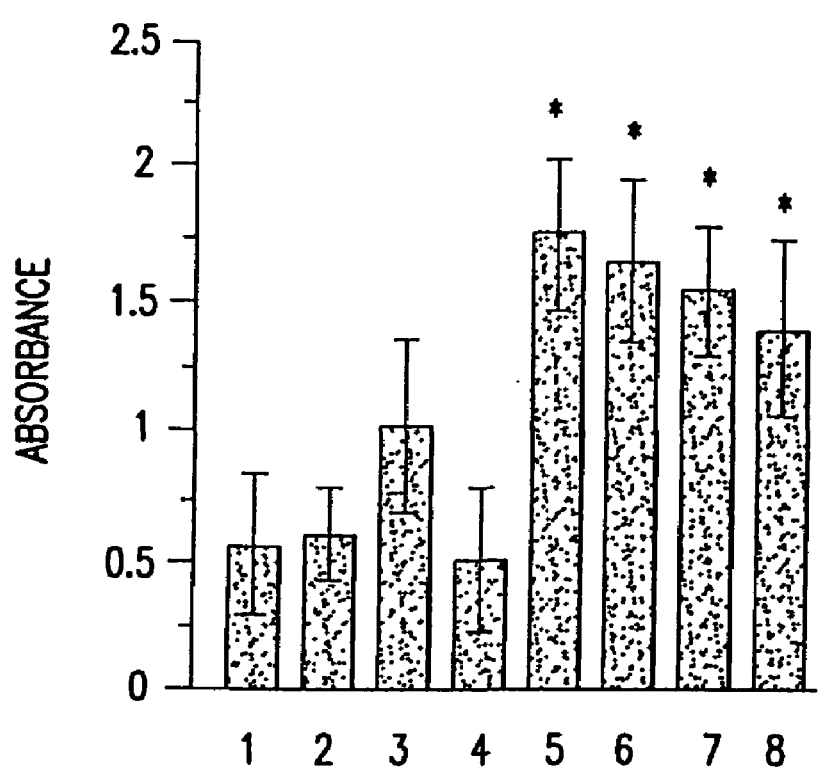

FIGS. 6A–C. Adhesion of normal and ADPKD epithelia to extracellular matrix proteins. FIG. 6A. Differential adhesion of human renal primary epithelial cell cultures derived from different nephron segments on type I collagen, (1000 cells, 48 hr.) in serum-free media. Lane 1, human fetal proximal tubule; lane 2, human fetal collecting tubule; lane 3, normal human adult proximal tubule; lane 4, normal adult thick ascending limb of Henle's loop; lane 5, normal adult collecting tubule; lane 6, autosomal dominant polycystic kidney disease cyst epithelia (ADPKD). * $p<0.01$. FIG. 6B. Differential adhesion (2,000 cells 12 hr) of primary cultures of ADPKD and normal adult thick ascending limb (NHTAL) epithelia on different matrix proteins. *$p<0.01$ ADPKD versus NHTAL on corresponding matrix. FIG. 6C. Comparative cell-type-dependent adhesion to type I collagen of human immortalized cell lines after differentiation at nonpermissive temperature 37° C. for 9 days, versus primary cultures. Lane 1, human fetal proximal tubule (HF PT) primary culture, passage 1; lane 2, HF PT immortalized, differentiated clonal line; lane 3, normal human fetal collecting tubule (HFCT) immortalized, differentiated clone; lane 4, immortalized differentiated NH PT clone; lane 5, ADPKD primary epithelial culture, P1; lanes 6, 7, and 8, immortalized differentiated ADPKD independent clones: 4,000 cells, 4 hr. Data are expressed as means±SEM. * $p<0.01$.

Figure 7A:
Figure 7B:
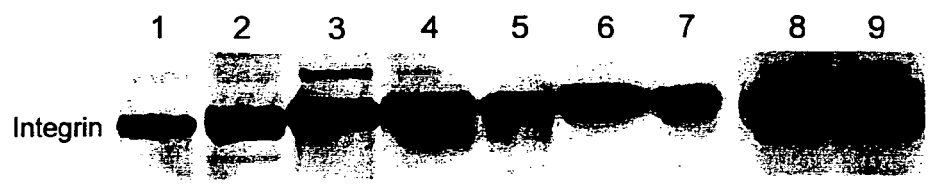
Figure 7C:
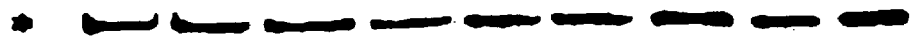
Figure 7D:
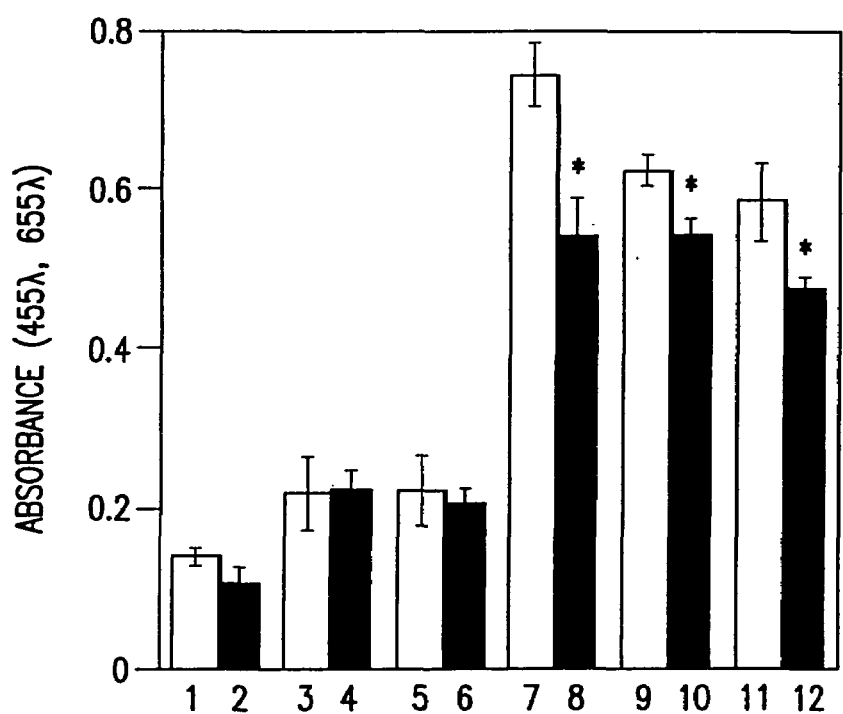

FIGS. 7A–D. α2β1 integrin and adhesion of ADPKD epithelia to type I collagen. FIG. 7A. Immunocytochemistry of α2β1-integrin (1: 250, Chemicon) in ADPKD epithelia, 48 hr. adhesion to type I collagen. Note extensive fibrillar staining at apparent points of focal contact with the substratum. FIG. 7B. Western immunoblot analysis of α2-integrin content of different cell types, 48 hr. adhesion to type I collagen. Lanes 1 and 2 HF PST; lanes 3 and 4 HF CT; lanes 5 and 6, NH PST; lane 7, NH TAL; lanes 8 and 9 ADPKD. FIG. 7C. * anti-actin to demonstrate equal protein loading, 20 mg per lane, equal exposure of blot. FIG. 7D. Differential effects of the α2β1-integrin blocking antibody, 6F1, on cell-type-dependent adhesion (4 hr.): incubation in the presence of 10 mg/ml monoclonal anti-α2β1-integrin blocking antibody, 6F1(filled bars) or irrelevant monoclonal antibody, PCNA (Signet, Deedham, Mass.) (open bars). Values expressed as mean +SEM. * $p<0.05$ by comparison to its pair. Adherence in the presence of 1% fetal bovine serum was similar to that in the presence of anti-PCNA. Lanes 1 and 2 HF PT; lanes 3 and 4 NH PST; lanes 5 and 6 NH CT; lanes 7–12 ADPKD, 3 independent kindreds.

Figure 8A:
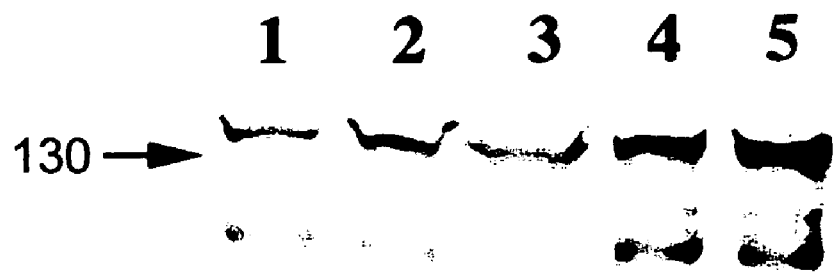
Figure 8B:
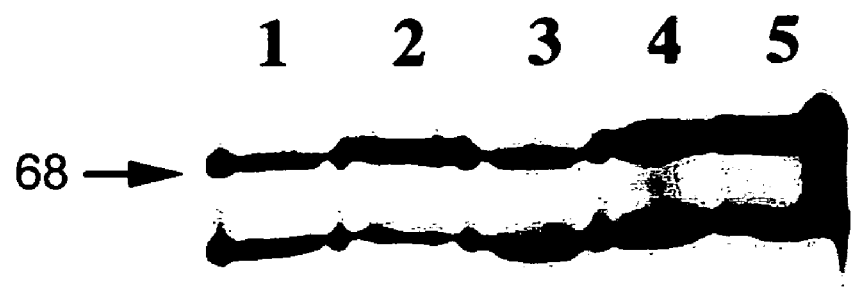
Figure 8C:
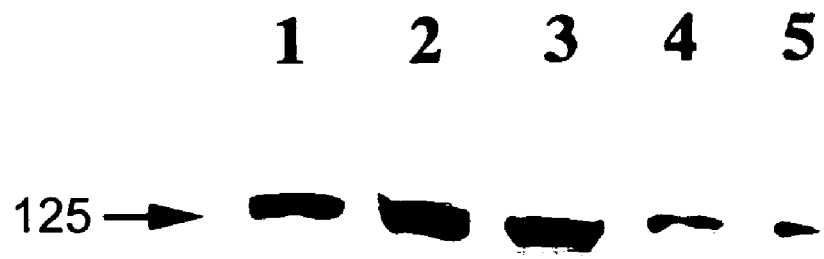
Figure 9A:
Figure 9B:
Figure 9C:
Figure 9D:
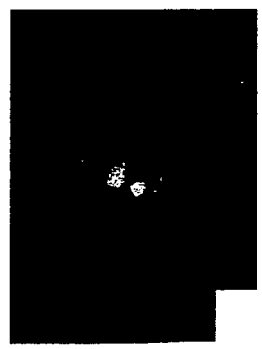
Figure 9E:
Figure 9F:
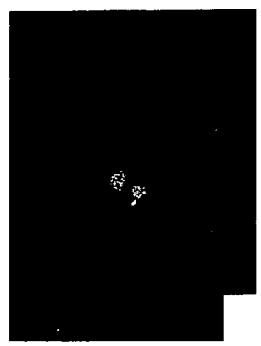
Figure 9G:
Figure 9H:
Figure 9I:
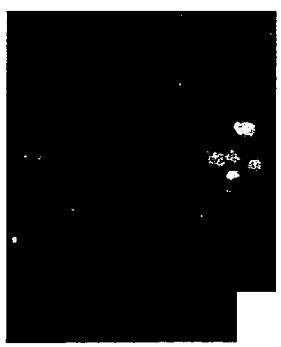

FIGS. 8A–C. Immunoblot analysis of focal adhesion proteins in cultured human renal tubule epithelia. FIG. 8A. Anti-vinculin monoclonal 1:7,500 (Sigma): 20 mg total protein per lane. Lane 1, normal adult proximal tubule epithelia; lane 2, normal adult thick ascending limb epithelia; lane 3, normal adult collecting tubule epithelia; lane 4, early stage ADPKD; lane 5, endstage ADPKD. Equal protein loading 20 mg per lane. Note increased content of vinculin in ADPKD epithelia. FIG. 8B. Anti-paxillin monoclonal, 1:10,000 (Transduction Laboratories). 20 mg total protein per lane. Lanes as in A. Note increased content of paxillin in ADPKD epithelia. Figure *C. Anti-pp125$^{FAK}$ monoclonal, 1:10,000 (Transduction Laboratories). 20 mg total protein per lane. Lanes as in A. Note decreased content of pp125$^{FAK}$ in ADPKD epithelia.

FIGS. 9A–I. Co-localization of polycystin-1 with integrins and associated proteins in ADPKD epithelia after short-term adherence to type I collagen. Confocal microscopy of double immunofluorescent labeling of ADPKD epithelial cells 4 hr. after adhesion to type I collagen. All cells were stained after incubation with 1:500 affinity purified, polyclonal anti-peptide C terminal polycystin-1 antibody (Panels B, E and H) followed by incubation with one of the following monoclonal antibodies: anti α2β1-integrin antibody, 1:100, (Chemicon), (panel A); anti-vinculin, 1:500, Sigma (panel D) or anti-paxillin, 1:250, (Sigma) (panel G). Monoclonal antibodies were visualized by coupling to FITC-labeled anti-mouse IgG and polyclonal antibody localization was visualized by rhodamine-coupled anti-rabbit IgG. Merging of the images (panels C, F and I) and resultant yellow/orange demonstrate co-localization of polycystin-1 with α2β1-integrin (C); vinculin (F) and paxillin (I). Plane of focus was at the level of contact of the cell with the substratum. X 250.

FIGS. 10A–F. Co-localization of polycystin-1 with integrin and associated proteins in normal human fetal collecting tubule epithelia after short-term adherence to type I collagen. Confocal microscopy of double immunofluorescent labeling of fetal collecting tubule epithelial cells 4 hr. after adhesion to type I collagen. Panel A, anti-α2β1-integrin; Panels B and E, anti-polycystin-1; Panel D, anti-vinculin; Panels C and F, merged images.

Figure 11A:
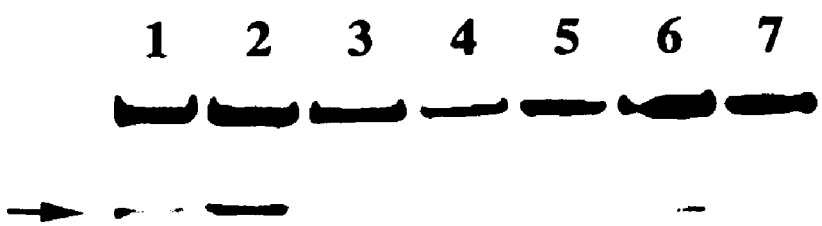
Figure 11B:
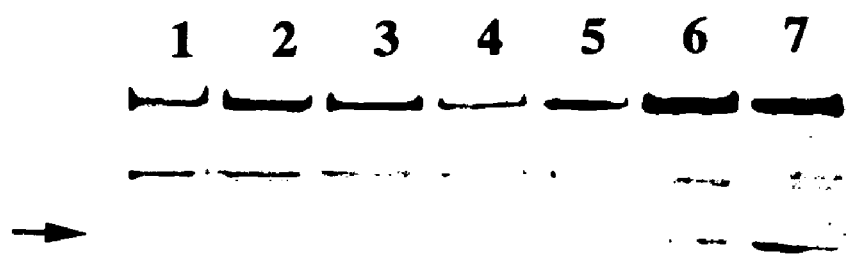
Figure 11C:
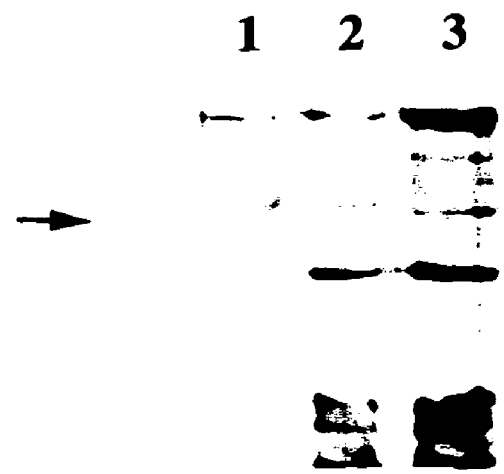

FIGS. 11A–C. Tyrosine phosphorylation of polycystin-1. FIG. 11A. Immunoblot analysis of polycystin-1 (1:12,500) in proliferating, adherent cultured ADPKD and normal epithelial cells. Arrow denotes position of 209 kDa marker. Note major band at >400 kDa and a single additional band of varying intensity at 225 kDa. Lane 1, ADPKD primary; lane 2, ADPKD immortalized clone; lane 3, NHCT primary; lane 4, NH TAL primary; lane 5, HF CT conditionally immortalized clone; lane 6, HFCT primary; lane 7, HFPT conditionally immortalized clone. Equal protein loading 20 mg per lane. FIG. 11B. Identical immunoblot as in A but stripped and reprobed with anti-phosphotyrosine antibody (RC-20, 1:2,500, Transduction Labs). Note immunoreactivity in the >440 kDa and 225 kDa bands, together with additional, lower molecular weight proteins. (Arrow shows position of 209 kDa marker). FIG. 11C. Immunoprecipitation of confluent ADPKD and normal epithelial cells with anti-phosphotyrosine antibody (RC-20) followed by Western immunoblot analysis with anti-polycystin-1 antibody shows a major >440 kDa band, attesting to the tyrosine-phosphorylation of polycystin-1. Lane 1, ADPKD primary epithelia; lane 2, NHCT primary epithelia; lane 3, HFCT primary epithelia.

Figure 12A:
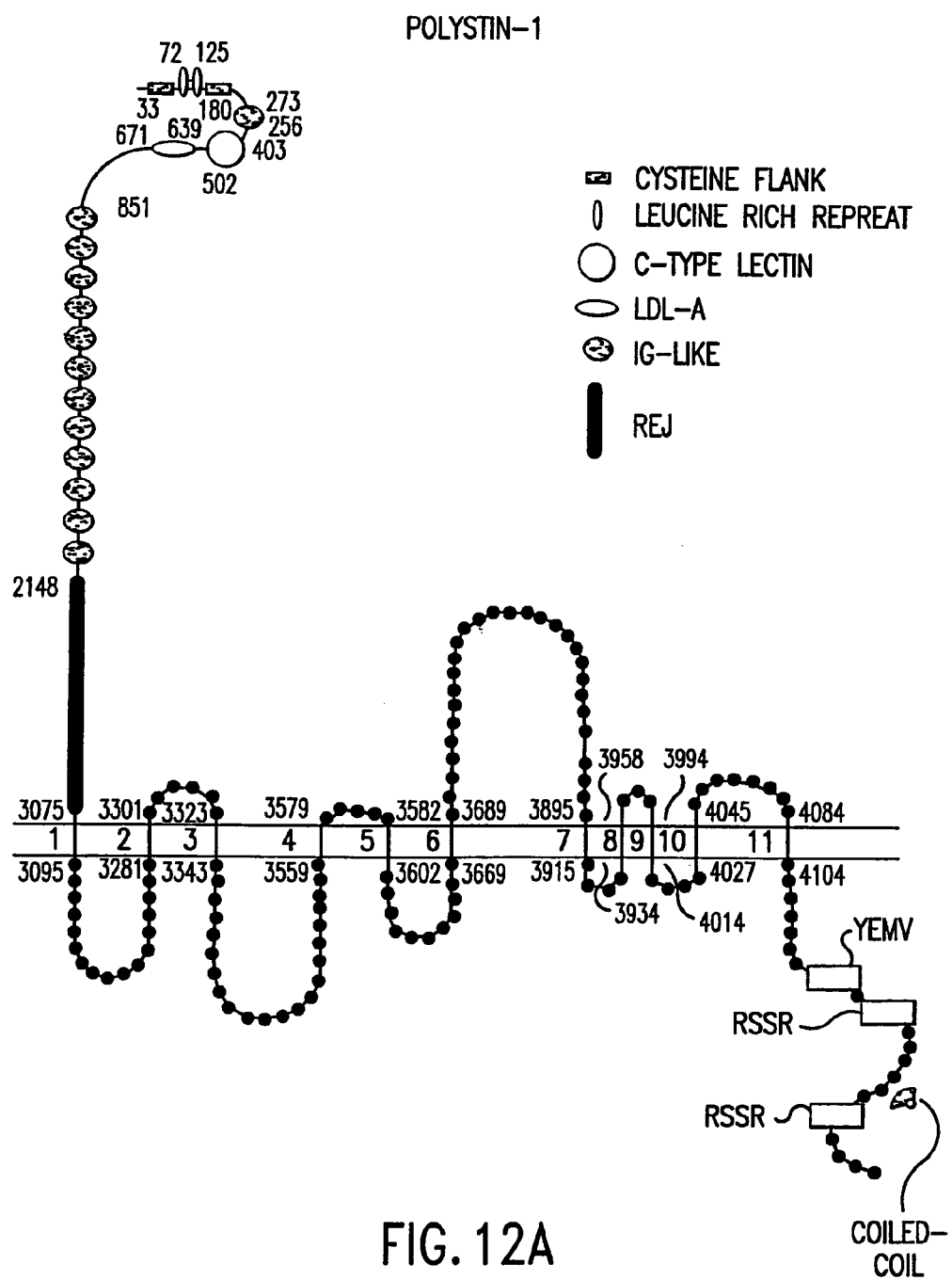
Figure 12B:
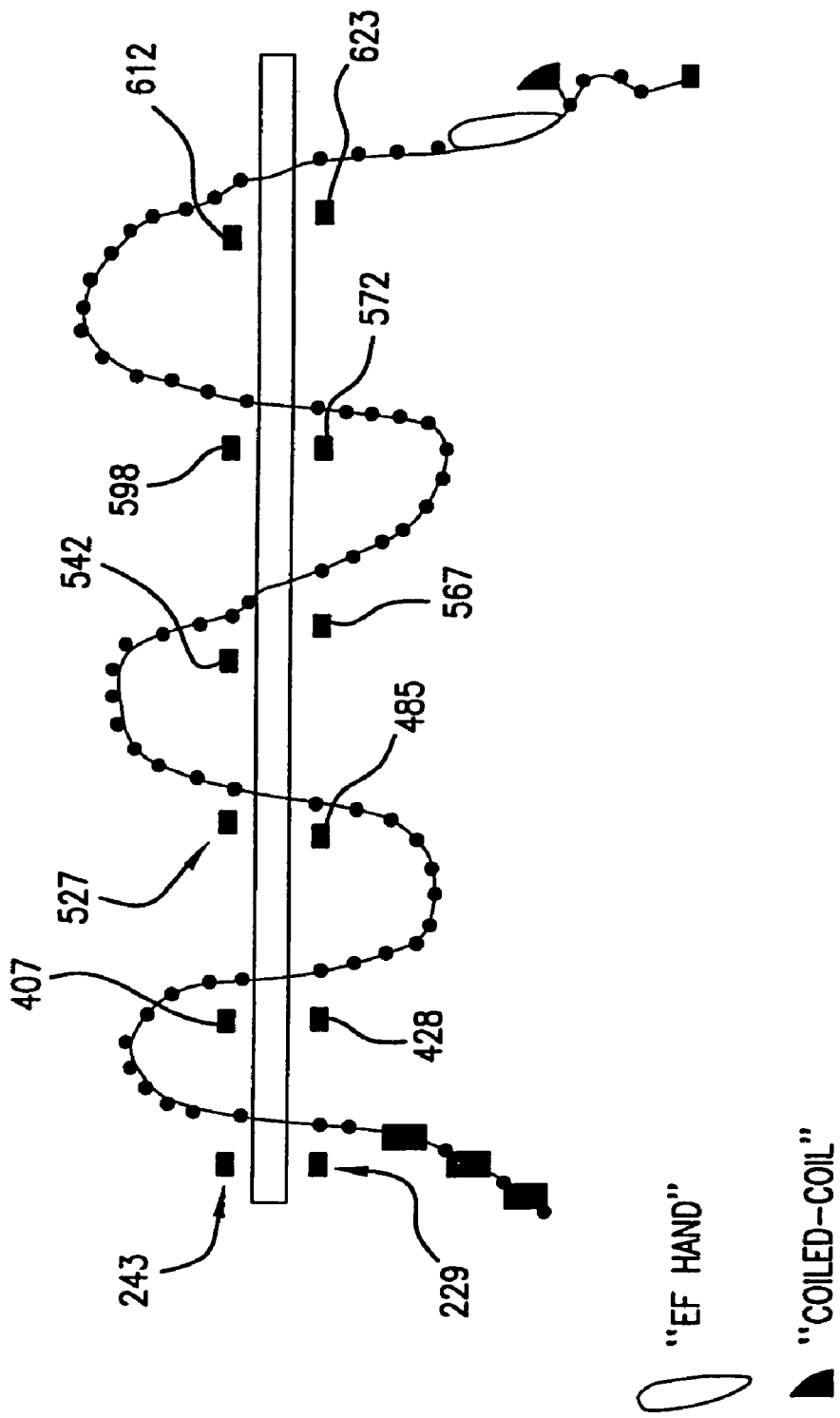
Figure 12C:
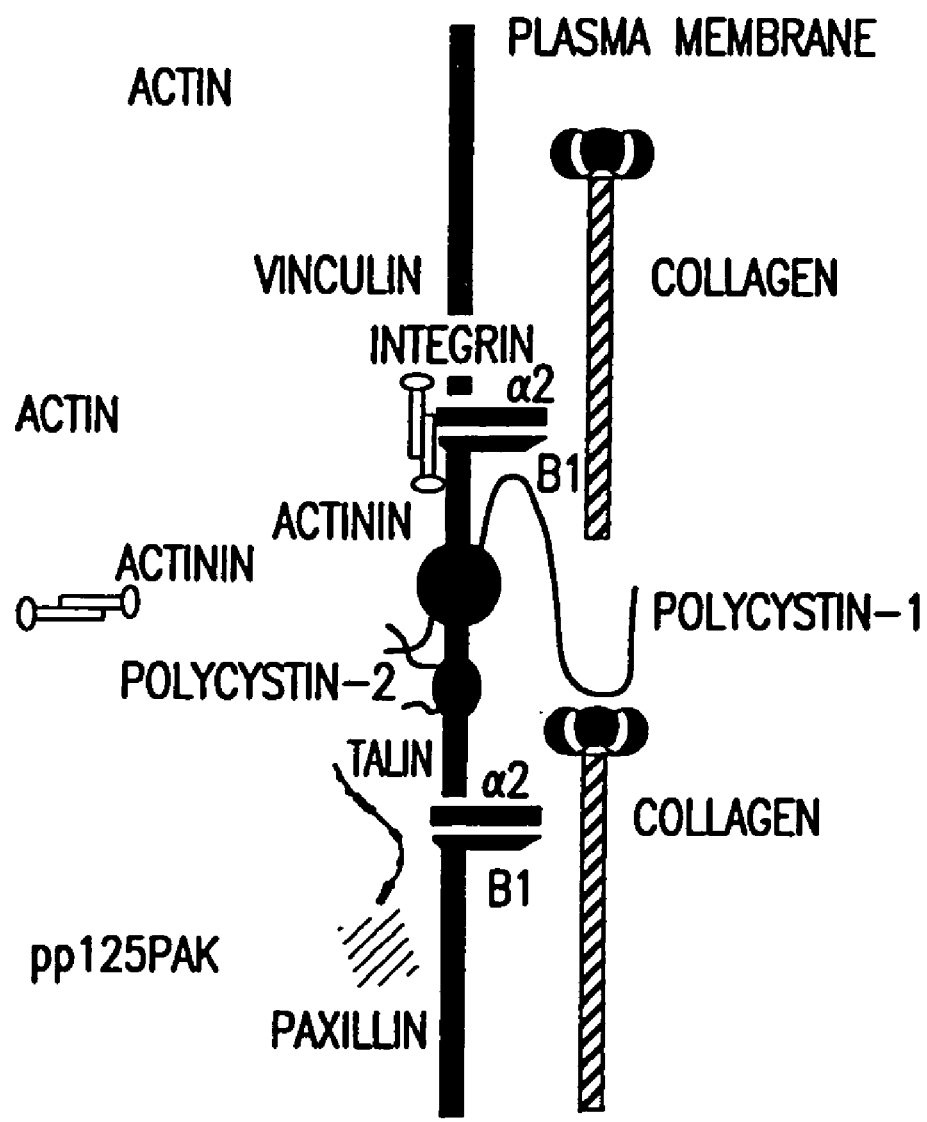

FIGS. 12A–C. Depictions of proposed structures of PKD-1 and PKD-2. FIG. 12A. Schematic representation of PKD-1 encoded gene product (Wilson et al., 1999, Exp Nephrol 7:114–124). FIG. 12B. Schematic representation of PKD-2 encoded gene product (Wilson and Guay-Woodford 1999, Seminars in Nephrology 19: 123–132) FIG. 12C. Model of polycystin-1 in a multi-protein complex at the cell membrane (Wilson et al., 1999, *Laboratory Investigation* 79:1–13).

Figure 13:
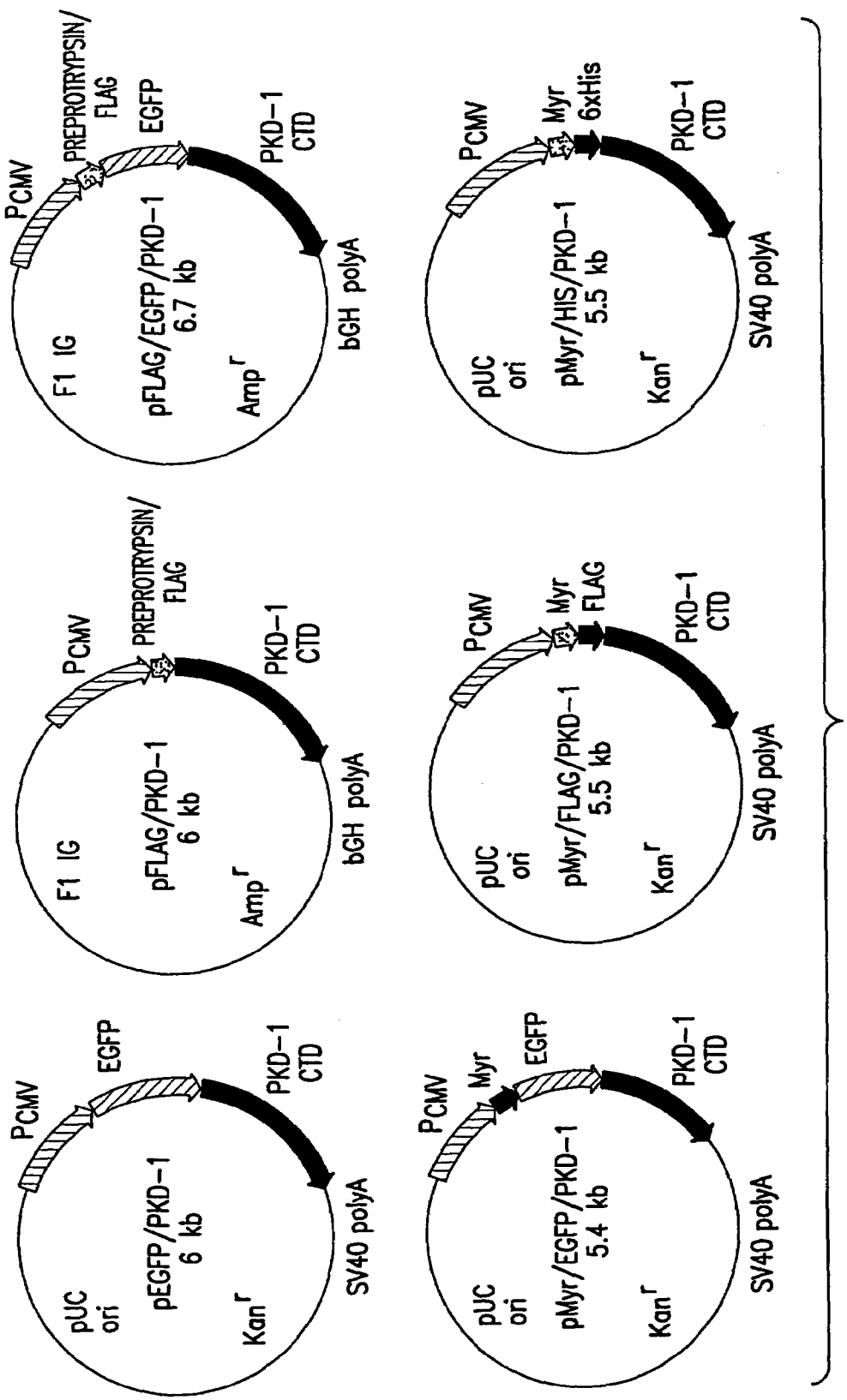
Figure 14A:
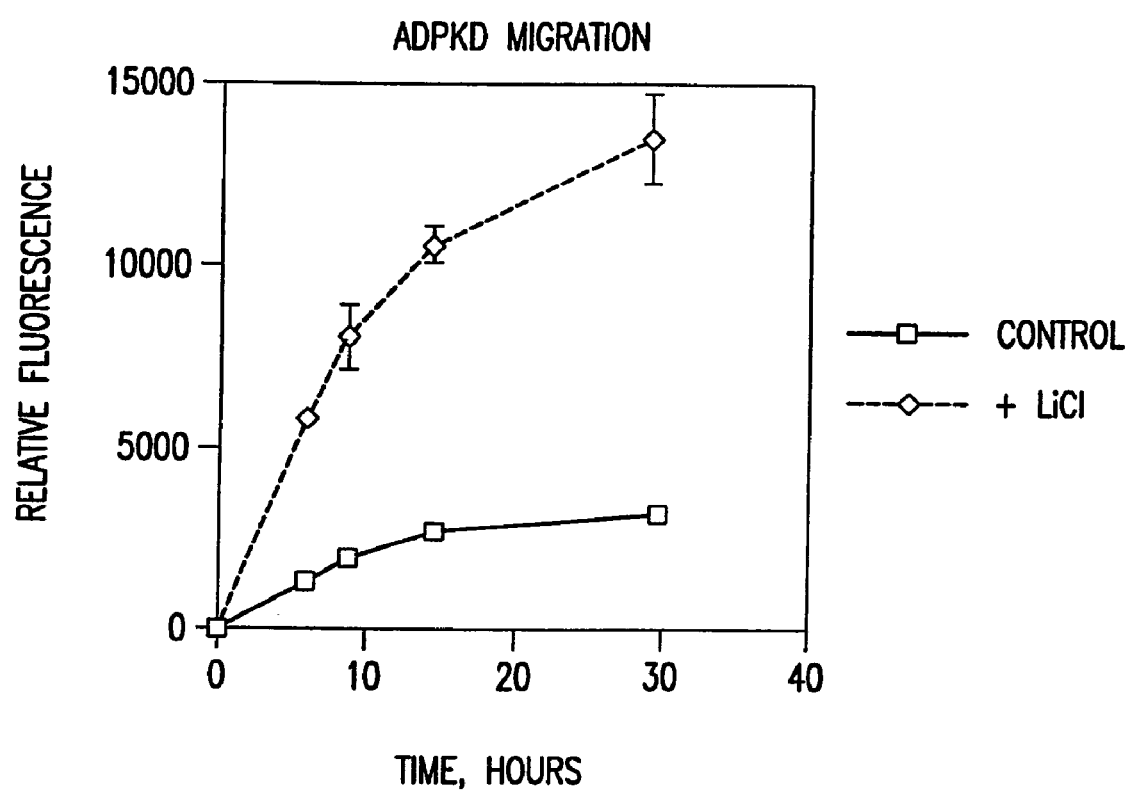
Figure 14B:
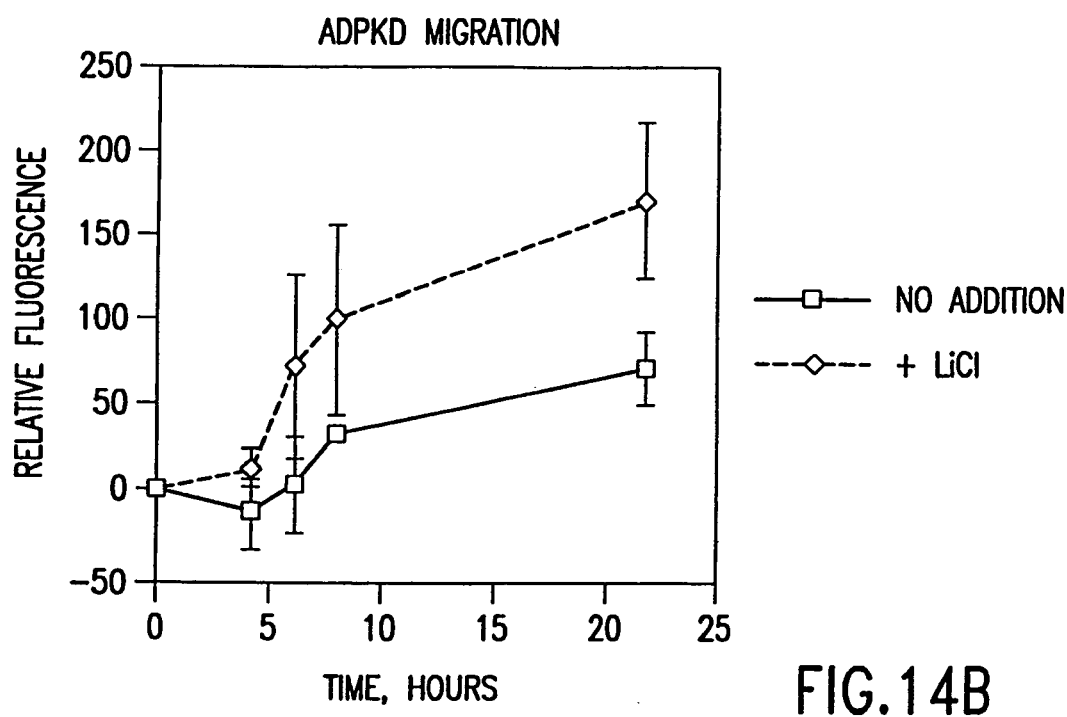
Figure 14C:
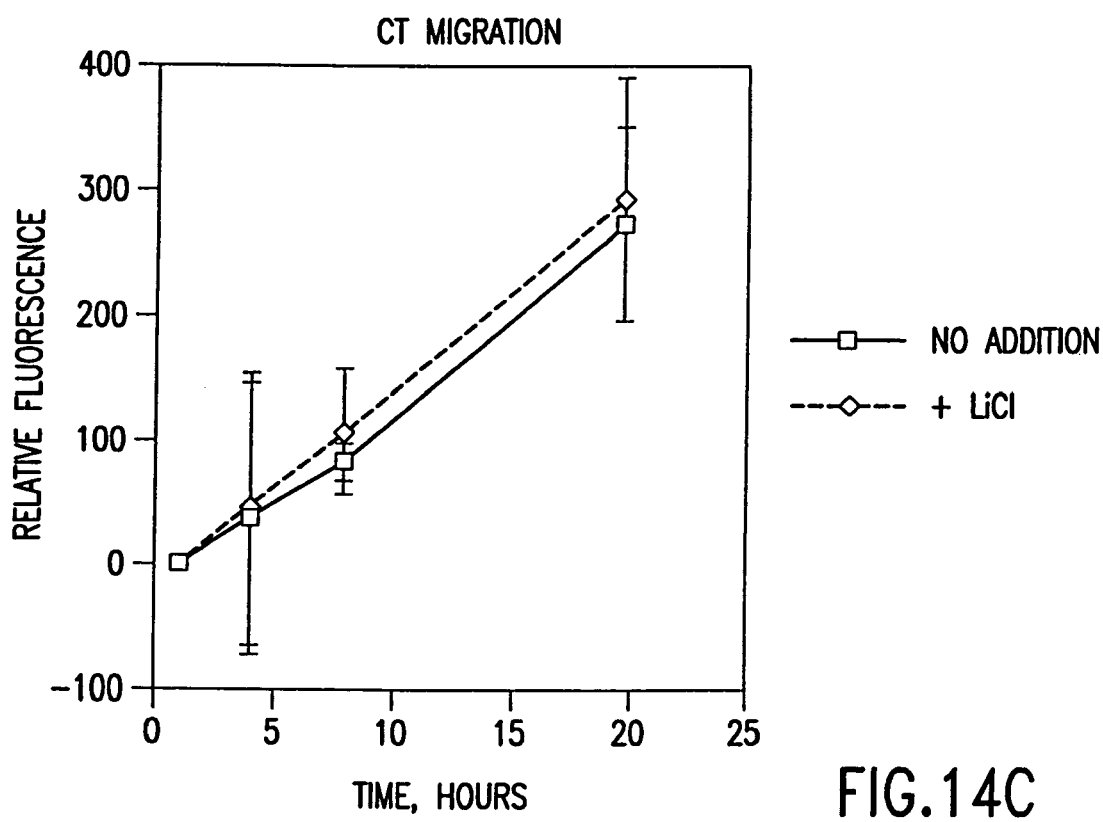

FIG. 13. PKD-1-epitope tagged eukaryotic expression vectors.

5. DETAILED DESCRIPTION OF THE INVENTION

The present invention relates to cell-based screening assays designed to identify agents that regulate the activity of polycystic kidney disease proteins (encoded by the PKD-1 and PKD-2 genes). The assay system of the invention is based on the use host cells that naturally express different forms of the polycystic kidney disease genes (PKD1 and PKD-2 and/or host cells genetically engineered to express different forms of the polycystic kidney disease genes (PKD 1 and PKD-2) including wild type, mutant, truncated, or epitope tagged PKD proteins. In specific non-limiting examples of the invention, human renal cells are engineered to express mutant or truncated forms of PKD protein and express a mutant phenotype which includes one or more characteristics associated with renal epithelial cells from patients with polycystic kidney disease, for example, increased adherence to type I collagen coated surfaces; apical expression of NaK-ATPase on the cell membrane; increased expression of β-2-NaK-ATPase; and decreased FAK incorporation into focal adhesion complexes, to name a few.

5.1 Generation of Recombinantly Engineered PKD Expressing Cells

In accordance with the invention, a cell-based assay system can be used to screen for agents that modulate the activity of PKD, and thereby modulate the mutant phenotype associated with polycystic kidney disease. To this end, host cells, such as human renal epithelial cells, are genetically engineered to express wild type, mutant, truncated or epitope tagged PKD proteins for use in the screening assays of the invention.

The cloning and characterization of the PKD-1 and PKD-2 genes from various species has been described (Mochizuki T et al., 1996, *Science* 272:1339–1342; The International Polycystic Kidney Disease Consortium, 1995, *Cell* 81:289–298; and Barr and Sternberg, 1999, *Nature* 401:386–389). In addition, mutant forms of the PKD receptor have been identified and described (European Polycystic Kidney Disease Consortium, 1993, *Cell* 75:1305–1315; Peral et al., 1996, *Am J Hum Genet* 58:86–96). For purposes of the present invention, host cells are genetically engineered to express any of the different forms of the PKD genes so long as the result is the expression of a mutant phenotype. Indeed, in some instances, over expression of wild-type PKD protein may result in expression of a mutant phenotype.

The nucleotide sequence coding for a PKD protein (PKD-1 or PKD-2), or fragment or other derivative thereof, can be inserted into an appropriate expression vector, i.e., a vector which contains the necessary elements for the transcription and translation of the inserted protein-coding sequence. In specific embodiments, the nucleotide sequence encoding a wild type or mutant PKD gene is cloned into an appropriate expression vector. Alternatively, nucleotide sequences encoding a functionally active domain of PKD can be cloned into an expression vector. For example, a fragment of PKD comprising functional domains such as an extracellular, transmembrane or intracellular C-terminal domain of the PKD protein can be expressed within a cell. In a specific embodiment, nucleotide sequences encoding the C-terminal domain of PKD, i.e., the C-terminal 226 and 200 amino acids of PKD-1 and PKD-2, respectively, are cloned into an appropriate expression vector. Such vectors may further comprise sequences that result in a physical association between the C-terminus of PKD and the plasma membrane. In a first nonlimiting embodiment, a myristylation sequence may be linked to the PKD encoding sequences to ensure targeting to the plasma membrane. Such myristylation sequences include the N-terminal myristylation sequence from pp60 src (Kaplan et al., 1988, *Mol Cell Biol* 8:2435–41). Further, a leader sequence, such as an N-terminal pre-protrypsin leader sequence, may be included to ensure membrane insertion of a truncated PKD protein.

In addition, PKD fusion proteins may be engineered to include a short stretch of residues corresponding to an epitope or other detectable label to facilitate subsequent biochemical and/or immunological analysis (e.g., "epitope tagging"). This is achieved by linking the sequence of the detectable tag to the PKD coding sequence. Suitable epitope tags include but are not limited to EGFP, FLAG, HA, 6-HIS, AU1, and green fluorescent protein (GFP) tags (see, Ausubel et al. (eds.), 1993, *Current Protocols in Molecular Biology, John Wiley &Sons*, N.Y.). An example of another detectable tag is green fluorescent protein.

Vectors encoding PKD proteins can be plasmid, viral or other vectors known in the art, for replication and expression in cells, including but are not limited to eukaryotic cells. Expression of a nucleic acid sequence encoding a PKD protein or peptide fragment may be regulated by any promoter/enhancer element known in the art to act in eukaryotic, preferably mammalian cells. Such promoters which may be used to control PKD expression can be inducible or constitutive. Such promoters include, but not limited to, the SV40 early promoter region (Bemoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.* 78:1441–1445), the regulatory sequences of the metallothionein gene (Brinster et al., 1982, *Nature* 296:39–42); prokaryotic expression vectors such as the beta-lactamase promoter (Villa-Kamaroff, et al., 1978, *Proc. Natl. Acad. Sci. U.S.A.* 75:3727–3731), or the tac promoter (DeBoer, et al., 1983, *Proc. Natl. Acad. Sci. U.S.A.* 80:21–25); promoter elements from yeast or other fungi such as the Gal 4 promoter, the ADC (alcohol dehydrogenase) promoter, PGK (phosphoglycerol kinase) promoter, alkaline phosphatase promoter. In addition, transcriptional control regions, which exhibit tissue specificity such as, for example, control regions which are active in renal epithelial cells may be used. The necessary transcriptional and translational signals can also be supplied by the native PKD gene and/or its flanking region.

The expression of the PKD protein may be regulated at the transcriptional level through the use of tightly control promoter systems that allow for inducible expression of the PKD proteins. Such promoters include, for example, those utilized in a tetracycline-controlled system (Gossen et al., 1993, *Trends Biochem Sci* 18:471–475; Barinaga, 1994, *Science* 265:26–28; Damke et al., *Methods in Enzymol.* 257:209–220).

Vectors to be used for expression of PKD may optionally comprise one or more selectable markers (e.g., an antibiotic resistance gene). Such vectors can remain episomal or become chromosomally integrated, as long as they can be transcribed to produce the desired cell lines expressing PKD.

Any of the methods well known to those skilled in the art can be used for the insertion of DNA fragments to construct expression vectors containing appropriate transcriptional/translational control signals and the PKD protein coding sequences. The methods to be used for construction of such vectors may include in vitro recombinant DNA and synthetic techniques and in vivo recombinants. Methods commonly known in the art of recombinant DNA technology which can be used are described in Ausubel et al. (eds.), 1993, *Current Protocols in Molecular Biology*, John Wiley &Sons, N.Y.

The present invention encompasses cell-based screening assays that utilize cell lines recombinantly engineered to express PKD proteins. In a preferred embodiment of the invention mammalian cells, such as primary or immortalized cultures of renal epithelial cells, are transfected with the recombinant vectors engineered to express PKD protein. Human renal cell lines may be derived from normal human adult kidney proximal tubules, normal human adult kidney collecting tubules, normal human adult kidney thick ascending limb tubules, normal human fetal kidney proximal tubules, normal fetal adult kidney collecting tubules, human adult autosomal dominant polycystic kidney disease epithelia and human adult autosomal recessive polycystic kidney disease epithelia. Such renal epithelial cells may be cultured in serum-free, cell-type specific media as described in Wilson et al. (1985, *Am. J. Physiol.* 248:F436–F443; and 1986, *Kidney Int.* 30:371–378) and immortalized as described in Racusen et al., (1995, *Kidney Int.* 48:536–543).

In another embodiments of the invention, the screening assays may be utilize non-human cells that contain a homolog of human PKD-1 or PKD-2 such as cells of *Caenorhabditis elegans*.

Various methods commonly known in the art for delivery of recombinant DNA to cells in tissue culture may be used. Such methods include electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene.

In addition to expression of introduced PKD proteins, host cells may be genetically engineered to express proteins known to, or suspected of, interacting with PKD proteins expressed within the cell. Such proteins include focal adhesion complex proteins such as FAK, paxillin, vinculin, talin, PKD-2 and *C. elegans* proteins such as unc-54 and act-5 and their human homologs, and the like. The tagging of such proteins will facilitate biochemical and immunological analysis of protein interactions for use in the screening assays of the invention. To this end, cells that endogenously express wild type or mutant PKD genes may be engineered to express epitope tagged PKD interacting proteins. Alternatively, cells may be co-engineered to express the various different forms of the PKD protein, as described supra, and epitope tagged PKD interacting proteins. Cells expressing such tagged proteins provide a tool for cell-based screening assays designed to identify agents capable of regulating, i.e., inhibiting or altering the affinity of, PKD protein interactions, and modifying the cellular phenotype. As a specific example, a human renal epithelial cell may be cotransfected with (i) a first gene encoding an epitope-tagged PKD-1 comprising the C-terminus and a membrane localization sequence and (ii) a second gene encoding an epitope tagged protein that interacts with PKD-1 at the cell membrane. The interaction of the proteins at the membrane may be visualized by immunological staining techniques. Such cells may be used to screen for agents that block the interaction of the proteins.

In a specific embodiment of the invention, several PKD-1-epitope tagged eukaryotic expression vectors were constructed and shown not only to transfect with high efficiency into normal renal epithelia and 293 cells, but also to be localized into basally located bodies at the cell membrane. The constructs include EGFP, FLAG and/or 6-His tags of the cytoplasmic portion of the C-terminal domain of PKD, with or without a myristylation sequence to ensure targeting to the plasma membrane. Also, similarly tagged constructs containing up to 5 transmembrane domains as well as the C-terminal domain (FIG. 13) were constructed and expressed in mammalian renal epithelia and 293 cells.

In addition to myristylation signals, membrane insertion of the FLAG tagged PKD-1 constructs was achieved via use of an N-terminal preprotrypsin leader sequence. Membrane insertion of the epitope tagged PKD-1 proteins, predicted to have 5 transmembrane (TM) domains and the CTD, was confirmed by immunohistochemistry. In contrast, the pEGFP/PKD-1 constructs which had no leader sequence were expressed as cytoplasmic proteins. The myristylated constructs appear to have the most efficient membrane localization to the basally located bodies of all of the constructs so far tested.

5.2. Assay Systems

In utilizing the cell-based assay systems of the invention, cells expressing PKD proteins are exposed to a test compound or to vehicle controls (e.g., placebos). After exposure, the cells can be assayed to measure the expression and/or activity of the components of the signal transduction pathway of the PKD receptor. For example, cells can be assayed for alterations in characteristics associated with renal cells from patients suffering from polycystic kidney disease such as adherence to type I collagen coated surfaces; expression of NaK-ATPase on the cell membrane; expression of β-2-NaK-ATPase; and FAK incorporation into focal adhesion complexes, proliferation, the inability to form tubular structures in a gel matrix and the expression of various fetal genes. In many instances, standard immunoassays which include Western blots, radioimmunoassays, ELISAs, immunoprecipitation assays and fluorescent immunoassays, to name but a few, may be utilized to detect changes in localization of PKD proteins and/or changes in interactions with other cellular proteins. In preferred embodiments, the assays are performed in 96-well plates to enable high-throughput screening and 96-well based scintillation counting instruments.

To confirm that any observed alterations in phenotype are due to a specific effect of the test compound on mutant PKD signal transduction, the test compound is also tested for its ability to alter the phenotype of cells expressing wild type PKD.

The cell based assays are designed to identify compounds which affect PKD-1 activity. Compounds that may affect PKD-1 activity include but are not limited to compounds that bind to the PKD-1 functional domains and either activate signal transduction (agonists) or block activation (antagonists). Compounds that affect PKD-1 activity by affecting PKD-1 gene expression, including molecules that affect transcription can also be identified using the screens of the invention. However, it should be noted that the assays described can also identify compounds that modulate PKD-1 signal transduction (e.g., compounds which affect downstream signaling events and participate in transducing the PKD-mediated signal). The identification and use of such compounds which affect signaling events downstream of PKD-1 and thus modulate effects of PKD-1 on the development of polycystic kidney disease are within the scope of the invention.

The compounds which may be screened in accordance with the invention include, but are not limited to proteins peptides, antibodies and fragments thereof, and other organic compounds (including, but not limited to, peptidomimetics) that bind to PKD-1 and either activate the activity of PKD-1 (i.e., agonists) or inhibit the activity of PKD-1 (i.e., antagonists). Compounds may include, but are not limited to, peptides such as, for example, soluble peptides, including but not limited to members of random peptide libraries; (see, e.g., Lam, K. S. et al., 1991, *Nature* 354: 82–84; Houghten, R. et al., 1991, *Nature* 354:84–86), and combinatorial chemistry-derived molecular library made of D- and/or L-configuration amino acids, phosphopeptides (including, but not limited to, members of random or partially degenerate directed phosphopeptide libraries; see, e.g., Songyang, Z. et. al., 1993, *Cell* 72:767–778). Other agents, not related to peptides, may also be screened, according to the invention.

To assay for a test compound's ability to regulate PKD activity, adherence to type I collagen coated surfaces may be assayed using tissue culture surfaces coated with type I collagen. Cells expressing mutant PKD have a 2- to 3-fold increase in adhesion to type I collagen coated surfaces as compared to wild type cells. Thus, the ability of a test compound to decrease levels of mutant cell adherence to type I collagen coated surfaces, below those levels seen with cells treated with a vehicle control, indicates that the test agent inhibits the signal transduction mediated by PKD.

To assay for cell adherence, cells may be plated onto 96-well cluster plates pre-coated with type I collagen, for a time sufficient to allow attachment in the presence of either a test agent or a vehicle control. Following attachment, the non-attached cells are removed by aspiration. Measurement of cell number attached to each plate is then carried out. For example, a colorimetric assay can be utilized to measure cell number attached to each well in the plate, read and quantitated using a microplate reader (Mossmann, 1983, *Imm Meth* 65:55–63).

Increased adhesion may also be determined using assays designed to detect the level of binding of cells to one another to form cluster of cells. The ability of a test agent to decrease the level of cell adherence, below those levels seen with cells treated with a vehicle control, indicates that the test agent inhibits the signal transduction mediated by PKD.

The ability of cells to form tubular structures may be evaluated by seeding the cells plus test agent in Matrigel or a comparable gel culture system.

Assays for expression of NaK-ATPase on the cell membrane may also be used in conjunction with genetically engineered cells expressing PKD for identification of agents capable of regulating PKD activity. Since PKD mutant cells express NaK-ATPase on their apical cell membranes, whereas normal renal epithelia have exclusively basal membrane located NaK-ATPase, this phenotype can be used to assess the ability of a test agent to reverse NaK-ATPase apical localization. Expression of NaK-ATPase in the cell membrane can be measured in the presence of a test compound or vehicle control, using for example, a fluorescent antibody against the NaK-ATPase sodium pump. Polarity of fluorescence may be easily assessed on a fluorescent reader. The ability of a test agent to decrease the level of NaK-ATPase expression on the apical cell membrane, below those levels seen with cells treated with a vehicle control, indicates that the test agent inhibits the signal transduction mediated by PKD.

In yet another embodiment of the invention, the ability of a test agent to decrease the expression of the β2 subunit of NaK-ATPase may be assayed to identify regulators of PKD activity. This assay is based on the observation that cells expressing mutant PKD express β-2 NaK-ATPase, while normal adult renal epithelial cells do not. Recombinantly engineered cells may be grown to confluence in 96-well cluster plates and the expression of the β2 subunit examined using a fluorescent detection system in the presence of a test agent or vehicle control. The ability of a test agent to decrease the level of β2 subunit of NaK-ATPase expression, below those levels seen with cells treated with a vehicle control, indicates that the test agent inhibits the signal transduction mediated by mutant PKD.

The incorporation of PKD proteins into focal adhesion clusters can also be used to assess the ability of a test compound to regulate the activity of mutant PKD. Other proteins known to localize to focal adhesion clusters include α2β1 integrin, vinculin, talin and paxillin. To this end, focal adhesion complex proteins, such as paxillin, vinculin and talin, may be genetically engineered so as to be labeled with epitope tags. Antibodies immunoreactive against the epitope tags may be used in the assays of the invention to determine whether a test compound is capable of altering the protein composition of focal adhesion complexes. For example, double labeling immunofluorescent studies may be conducted to determine whether PKD co-localizes in the cell with α2β1-integrin, vinculin and paxillin using fluorescent labeled antibodies immunoreactive against each of the proteins. Numbers of focal adhesion clusters can be assessed by reading on a fluorescent plate reader and the location of focal clusters can be assessed microscopically.

In normal cells, focal adhesion kinase (FAK) is incorporated into focal adhesion complexes, while in mutant cells FAK fails to be incorporated into such complexes. Thus, agents may be screened for their ability to increase the level of FAK incorporated into focal adhesion complexes. To this end, FAK may be genetically engineered so as to be labeled with epitope tags such as FLAG, HA, green fluorescent protein or 6-His. Antibodies immunoreactive against the epitope tags may be used in the assays of the invention to determine whether a compound is capable of altering the localization of FAK in focal adhesion complexes. For example, labeling immunofluorescent studies may be conducted to determine whether FAK localizes to focal adhesion complexes.

5.3. Use of *C. elegans* Model System

Compounds identified via cell based assays such as those described herein may be useful, for example, in elaborating the function of PKD gene products and for ameliorating the symptoms associated with polycystic kidney disease. Assays for testing the efficacy of compounds identified in the cell-based assays can also be tested in model systems for polycystic kidney disease based on other types of organisms. Such model systems may be used as test substrates for the identification of compounds that may be effective in treating polycystic kidney disease.

To this end, *C. elegans* can be used as a model system. The *C. elegans* genome has homologs of both the human PKD-1 and PKD-2 genes. Thus, the *C. elegans* provides a new model system for the study of essential genes (including the polycystic kidney disease genes PKD-1 and PKD-2) in the development and maintenance of the renal epithelia of the mammalian nephron. An understanding of the effects of PKD-1 and PKD-2 mutations in *C. elegans* will provide additional insights into the function of these genes and form the basis for a screening approach for the validation of compounds identified in the cell based assays with potential therapeutic activity in the treatment of human polycystic kidney disease. For example, a mutated form of PKD-1 or PKD-2 may be introduced into *C. elegans* cells or organisms and its effect on excretory cell function and cell attachment bodies evaluated. Such genetically modified C. elegans cells or organisms may be used to screen for agents that reverse the effects of the mutation.

In addition, use of a yeast two-hybrid screen may be used for the identification of C. elegans PKD-1 and PKD-2 interacting proteins. To confirm that the interacting proteins from C. elegans reflect a molecular interaction that parallels that of PKD proteins in human cells, full length cDNA clones representing the human homologs of the identified PKD interacting proteins may be obtained, sequenced and subcloned into a suitable expression vector. Antisera may be prepared against selected peptides derived from the open reading frames of the obtained cDNAs. To validate PKD-1 and PKD-2 protein interactions identified in the C. elegans yeast two-hybrid screen, renal cells engineered to express tagged human homologs of the PKD-1 and PKD-2 interacting proteins may be used to determine whether there is co-localization with PKD proteins.

To this end, renal epithelial cells engineered to express tagged PKD polypeptides may be used to determine whether the putative interacting proteins colocalize with the PKD protein products. Such studies may be conducted using standard immunoassays which include western blots, radio-immunoassays, ELISAs, inimunoprecipitation assays and fluorescent immunoassay, to name but a few. For example, co-immunoprecipitation of PKD interacting proteins and PKD proteins can be demonstrated using PKD-1 and PKD-2 antisera in selected human renal epithelial cell lines engineered to express PKD-1 and PKD-2 proteins The selected cells may also be transfected with epitope-tagged putative PKD interacting proteins. Additionally, PKD immunoprecipitations followed by Western immunoblotting using antisera raised against PKD interacting proteins in non-transfected renal cells may be performed to determine in protein interactions occur at physiological levels of protein expression. Identification of such specific protein interactions provides a target for drug screening.

C. elegans proteins that interact with PKD proteins in a manner that parallels PKD interactions in human renal cells may be used as a basis for a primary screen, in C. elegans, to identify agents that modulate the protein interaction. The ability of modulating agents identified in the C. elegans screen to modulate the interacting human homologs may then be confirmed using human renal cell lines transfected according to the invention.

6. EXAMPLE

Expression of PKD-1 in Human Tissues and Renal Epithelial Cells

The expression of the PKD-1 encoded protein "polycystin-1" in human tissues and renal epithelial cell lines and the mechanisms of adhesion of polycystin-1-expressing renal epithelial cells to matrix proteins was examined. PKD-1 mRNA is highly expressed in normal human fetal kidneys in the ureteric bud epithelium, as well as in the cystic epithelial cells of ADPKD kidneys (Wilson, 1997, *Am J Physiol* 272:F434–F442; Ward et al. 1996, *Proc Natl Acd Sci USA* 93:1524–1528; Geng et al. 1996, *J Clin Invest* 98:2674–2682). Previously devised techniques for generating pure cell lines of different human renal tubule epithelial cell types from normal adult and fetal kidneys, as well as from ADPKD cysts have been described (Wilson et al., 1985, *Am J Physiol* 248:F436–F443; Racusen et al., 1995, *Kid Int* 48:536–543; Cuppage et al., 1980, *Kid Int* 17:372–381). For the present studies, polycystin-1-expressing normal and ADPKD epithelial cell lines were used to study the biological function of polycystin-1 in response to matrix adhesion.

6.1. Materials and Methods

6.1.1 Tissue Culture

Primary and immortalized cells of normal fetal and adult proximal tubules, thick ascending limbs of Henle and collecting tubules and of ADPKD cyst epithelia were cultured in serum-free, cell-type specific media as described previously (Wilson et al., 1985, *Am J Physiol* 248: F436–F443, Wilson et al., 1986, *Kidney Int* 30:371–378 Racusen et al., 1995, *Kidney Int* 48:536–543). Cells from each cell type were immortalized by retroviral transduction of the SV40 tsA58 U19 vector and selection in G418 at 33° C. for 6 weeks. Clonal, immortalized ADPKD cell lines have a truncating mutation in exon 26 (Harris, P.C., personal communication). Prior to experimentation all immortalized cell lines were cultured for 7–14 days at 37° C., to terminate proliferation and maximize differentiation.

6.1.2 Recombinant Fusion Protein Production

A fusion protein containing the C-terminal of human polycystin-1 (amino acids 4105–4303) was amplified by PCR from a 2 kb PKD1 cDNA clone obtained by RT-PCR and subcloned into PET-32 LIC (Novagen). The fusion protein was expressed in BL-21 (D3) plys S competent cells and purified using S-tag affinity chromatography.

6.1.3. Immunocytochemistry

The anti-polycystin-1 antibody was raised in rabbits against a purified synthetic 31 amino acid peptide corresponding to amino acids 4161–4191 in the predicted intracellular portion of polycystin-1, proximal to the C-terminal: sequence LPSRSSRGSKVSPDVPPPSAGSDASHPSTSS (SEQ ID NO: 1). Antiserum specificity was confirmed by Elisa, immunoblot and immunocytochemical analyses, before and after affinity purification; by lack of staining with pre-immune sera and competition of immunoreaction by preadsorption with the appropriate peptide. Immunocytochemistry was carried out using an avidin-biotin-peroxidase system (Vectastain, Vector Laboratories) and aminoethylcarbazole as chromogen 9 (red color). Staining patterns were identical when carried out on frozen and paraformaldehyde (4%)-fixed material. 1:500 dilution of anti-polycystin-1 was used.

6.1.4. Adhesion Assays

Epithelial cell adhesion to extracellular matrix substrates was determined by plating of 1,000–4,000 cells per well of 96-well cluster plates precoated with matrix protein as indicated. Cells were allowed to adhere under serum-free conditions for varied lengths of time (4 hr.–48 hr.), non-adherent cells removed by washing and adherent cell number determined by a linear calorimetric assay (Promega Cell titer 96™ AQ, 4–24 hr. incubation with 3-(4,5-dimethylthiazol-2-yl)-5-(3-carboxy methoxyphenyl)-2-(4-sulphonyl)-2M-tetrazolium, (MTS) and phenazine methosulfate (PMS).

6.1.5 Double Immunofluorescent Labeling

Cells on coverslips were washed and fixed in freshly prepared, ice-cold 4% paraformaldehyde for 3 min, washed 3 times, 3 min each with PBS and then subjected to double-labeling with polyclonal anti-polycystin coupled to anti-rabbit-IgG-rhodamine and monoclonal anti-α2β1-integrin (1:100, Chemicon), or vinculin (1:500, Sigma), or paxillin (Sigma, 1:250), coupled to anti-mouse-IgG-FITC.

6.1.6. Western Immunoblot Analysis

SDS, NP-40 and Triton X-100 lysates were prepared from subconfluent and confluent monolayers of cell cultures washed in PBS containing a comprehensive protease inhibitor cocktail and vanadate. Equal amounts of protein (20 mg) were loaded per lane and separated by SDS-PAGE, transferred to nitrocellulose or nylon membranes and blotted with anti-polycystin (1:12,500), anti-phosphotyrosine, RC-20, (Transduction Laboratories, 1:2,500), anti-a2 integrin (Chemicon, 1:2,000); anti-actin (Chemicon, 1:2,500); anti-vinculin (Sigma, 1:7,500; anti-paxillin (Transduction, Laboratories, 1:10,000) and anti-FAK (Transduction Laboratories, 1:10,000).

6.1.7. Immunoprecipitations

Immunoprecipitations were carried out on NP40/Triton X-100 cell extracts (5×100 mg) containing protease inhibitors, using anti-PKD-1 and anti-phosphotyrosine antibodies added to precleared Protein A/G PLUS agarose beads for 1 hr. and 4° C. After 3 washes with immunoprecipitation buffer the pellet was resuspended in sample buffer and subjected to SDS-PAGE.

6.1.8 Statistics

Data were expressed as mean±standard error and groups were subjected to analysis of variance.

6.2 Results

Figure 3A:
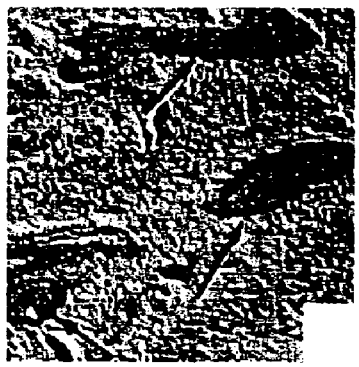
Figure 3B:
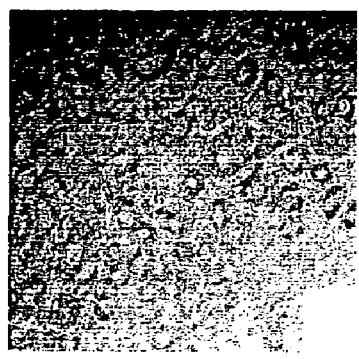
Figure 3C:
Figure 3D:
Figure 3E:
Figure 3F:
Figure 3G:
Figure 3H:
Figure 10A:
Figure 10B:
Figure 10C:
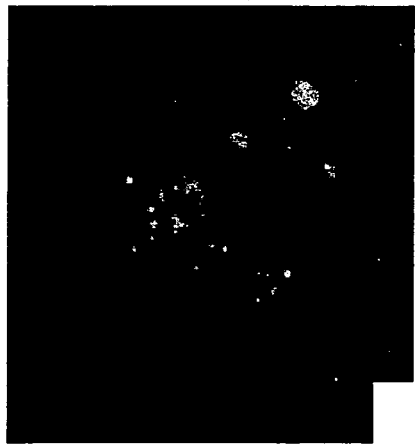
Figure 10D:
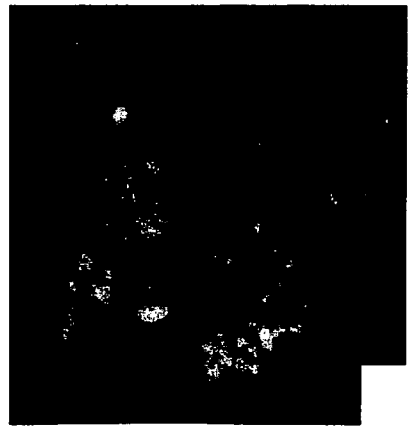
Figure 10E:
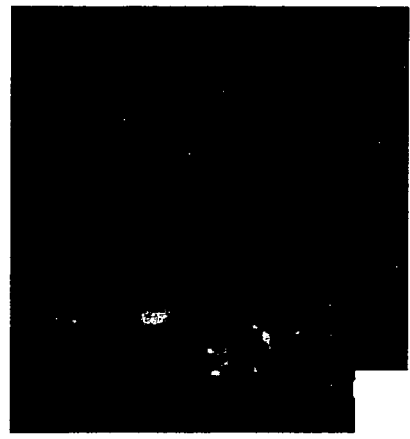
Figure 10F:

A 31 amino acid peptide polyclonal antibody, corresponding to amino acid residues 4161–4191 in polycystin-1 was raised in rabbits, affinity purified and characterized for its specificity (FIGS. 1 and 2). The anti-polycystin-1 antibody recognized a fusion protein containing the C-terminal, intracellular portion of polycystin-1 (residues 4105–4303) while the pre-immune serum did not (FIG. 1A). In addition, a single band of anticipated >440 kDa molecular weight was detected in cell lysates from human fetal collecting tubule cell lines, while pre-immune serum detected no bands (FIG. 1B). This antibody was high titer both for Western immunoblot analysis where it was used at 1:12,500 dilution and also for immunohistochemical analyses where it was used at 1:500 on paraformaldehyde fixed, paraffin embedded tissue sections (FIGS. 2A–C) and 1:1,000 on cultured cells (FIG. 2D). Immunoreactivity was dramatically reduced or absent after competition by preadsorption with the purified peptide (FIGS. 2E–H). No immunoreactivity was seen in tissue sections or cells after incubation in preimmune sera (FIGS. 3D and H). This antibody could also be used for immunoprecipitation analysis detecting a >440 kDa band which was absent from immunoprecipitations carried out with preimmune sera (FIG. 10A).

Primary cell strains and immortalized cell lines of normal and ADPKD renal epithelia were characterized with regard to their polycystin-1 expression by immunocytochemical and Western immunoblot analyses (FIGS. 3 and 4). The cells selected for study also showed cell-type specific marker expression. Stationary, confluent cultures of fetal collecting tubule epithelia showed characteristically high levels of normal polycystin-1 (FIG. 3E); normal adult collecting tubules showed low levels of expression (FIG. 3F); and ADPKD epithelia showed high levels of expression of polycystin-1 (FIG. 3G). ADPKD epithelia from 10 different kindreds showed high levels of expression by immunocytochemistry and Western immunoblot analysis, using our C-terminal region antibody. This was also the case in multiple independent immortalized clonal ADPKD cell lines established from a single sample known to contain a mutation at exon 16 and to predict a truncated protein (Harris, P.C. personal communication). This finding of high level expression of polycystin-1 protein expression in ADPKD cystic epithelia is consistent with the findings of several other laboratories using monoclonal and polyclonal antibodies raised against a variety of-terminal to C-terminal epitopes in human disease as well as in mice with a heterozygous PKD1 mutation introduced by targeted gene disruption (Ward et al., 1996, *Proc Natl Acad Sci USA* 93:1524–1528; Griffin et al., 1996, *Proc Assoc Am Physicians* 108:185–197; Peters et al., 1996, *Lab Invest* 75:221–230; Geng et al., 1996, *J Clin Invest* 98:2674–2682; Wilson, 1997, *Am J Physiol* 272:434–F442; Van Adelsberg et al., 1997, *Am J Physiol* 272:F451–F459; Weston et al., 1997, *Histochem J* 29:847–856; Ong et al., 1999, *Am J Pathol* 154:1721–1729; Lu et al., 1999, *Nat Genet* 21:160–161). This expression pattern of polycystin-1, therefore, mirrored those seen in normal fetal, adult and ADPKD tissues (FIG. 4A).

6.2.1 Matrix Adhesion in ADPKD

Previous studies have identified a variety of structural abnormalities in the extracellular matrix of human ADPKD kidneys and in matrix protein synthesis and turnover of cultured ADPKD epithelial cells in vitro (Wilson and Falkenstein, 1995, The Pathology of human renal cystic disease. In: Dodd S M, editor. Current topics in pathology, vol 88. Heidelberg: Springer-Verlag, 1–50; Wilson et al., 1996, Pathogenesis of polycystic kidney disease: Altered cellular function. In: Watson M L and Torres V E, editors. Polycystic kidney disease. Oxford: Oxford Medical Publications; Liu et al., 1992, *Am J Physiolol* 263:F697–F704). In initial studies, it was also noted that ADPKD epithelia were more adherent in vitro than their normal counterparts and that the degree of adhesion influenced subsequent epithelial cell proliferation (Wilson and Sherwood, 1991, *Kidney Int* 39:450–463; Wilson et al., 1992, *J Cell Physiol* 150:360–369). These observations have now been re-examined, expanded and evaluated with respect to cell-type and matrix protein specificity using a highly reproducible, quantitative adhesion assay (FIG. 5). FIG. 5A is a typical representative profile of adhesion for primary epithelial cell strains derived from different segments of the nephron. Twenty separate experiments were conducted at 12–24 and 48 hour time-points, plating 2,000 and 1,000 cells respectively. An additional set of 12 experiments was carried out measuring adhesion after 15 min, 30 min, 90 min and 4 hr. adhesion plating 2,000–5,000 cells per well. It was consistently observed that ADPKD cell lines expressing high levels of polycystin-1 (FIG. 5A, lane 6) were significantly (2 to 3-fold) more adherent than fetal or adult proximal tubule epithelia (PT FIG. 5A, lanes 1 and 3), adult thick ascending limb epithelia (TAL, FIG.

5A, lane 4) or adult collecting tubule epithelia (CT, FIG. 5A, lane 5) expressing lower levels of normal polycystin-1. Fetal collecting tubule epithelia (HFCT) expressed intermediate to high levels of polycystin-1 (FIG. 3E, FIG. 4B, lanes 1 and 2) and showed intermediate levels of adhesion to type I collagen (FIG. 5A, lane 2).

The specificity of this adhesion preference was demonstrated by a differential effect with regard to the type of extracellular matrix protein used in the assay. Adherence to uncoated tissue culture plastic ("none") and to type I collagen were the most discriminatory and significantly greater than adhesion to type IV collagen or to fibronectin (FIG. 5B). No difference in the adhesion of normal and ADPKD cells was seen on laminin substrates. This finding was of interest since type I collagen is a major component of the immediate extracellular matrix of both ADPKD and fetal ureteric bud epithelia, in vivo (Ekblom, 1989, *FASEB J* 3:2141–2150). By contrast, normal adult renal epithelia are in immediate contact with an intact basement membrane, which contains type IV collagen and laminin, not type I collagen which is restricted to the interstitium. This 2 to 3-fold increase in adhesion to type I collagen by ADPKD epithelia was also seen in conditionally immortalized ADPKD clonal cell lines (FIG. 5C, lanes 6, 7 and 8), suggesting this is a widespread cellular alteration in ADPKD cyst lining epithelia. Again, HFCT conditionally immortalized clones showed higher levels of attachment than other normal renal epithelial cell types (FIG. 5C, lane 3). These results show that the same patterns of differential adhesion to type I collagen were retained in conditionally immortalized cell lines derived from human renal epithelia cultured at the non-permissive temperature of 37° C., conditions under which normal differentiation characteristics have been demonstrated by marker analysis (Racusen, 1995, *Kidney Int* 48:536–543; Wilson 1999, In vitro methods in renal research. In: Barrat T M, et al., editors. Pediatric nephrology, 4$^{th}$ ed. Baltimore: Lippincott Williams & Wilkins, 269–281).

6.2.2. Role for α2β1 Integrin in Adhesion

A potential role for α2β1 integrin in this adhesion difference was studied since this heterodimeric complex has been shown to act as a receptor for type I collagen (Hynes, 1992, *Cell* 69:11–25). Immunocytochemical analysis showed that ADPKD epithelia grown to confluence on type I collagen, stained intensely for α2β1 integrin and demonstrated a focal pattern of distribution characteristic of accumulation at points of cell contact with its substratum, seen as ridges of reaction product at the plane of cell-substrate contact (FIG. 6A). In addition, an approximately 2-fold increase in a2-integrin content in adherent ADPKD versus adherent normal epithelia was seen by Western immunoblot analysis of whole cell extracts (FIG. 6B, lanes 8 and 9) potentially implicating an integrin-mediated mechanism for the increased adhesive properties of ADPKD epithelia. Functional involvement of a2131 integrin in polycystin-related adhesion was also suggested by inhibition of adhesion of ADPKD epithelial cells by a blocking antibody against α2β1 integrin, "6F1"(Coller et al, 1989, *Blood* 74:182–192; FIG. 6C lanes 8, 9 and 10) but not of normal cells (FIG. 6C, lines 2, 4 and 6).

Western immunoblot analysis of intracellular proteins which are known to interact with α2β1 integrin in other cell systems, also showed some trends to quantitative changes in total cell expression levels in confluent cells when levels in normal epithelia were compared with those in ADPKD epithelia after plating of the same numbers of cells on type I collagen and allowing adhesion for identical lengths of time. Vinculin (FIG. 7A) and paxillin (FIG. 7B) were approximately 2-fold increased in ADPKD cells (lanes 4 and 5), while focal adhesion kinase (pp125$^{FAK}$) was apparently decreased in ADPKD epithelia by comparison to normal renal epithelial cells (FIG. 7C, lanes 4 and 5).

6.2.3 Colocalization of Polycystin-1 With Focal Adhesion Plaque Proteins

The finding of a specific alteration of α2β1-integrin function and quantitative increases in α2β1-integrin, vinculin and paxillin in ADPKD epithelial cells suggested the possibility that polycystin-1 might interact directly with α2β1-integrin at sites of cell attachment to the underlying matrix. To test this notion, double labeling immunofluorescence and confocal microscopy was carried out using anti-polycystin-1 antibody raised in rabbit and anti-α2β1-integrin mouse monoclonal antibody. These studies (FIGS. 8A–C) using rhodamine conjugated secondary antibody for polycystin-1 and fluorescein isothiocyanate (FITC) conjugated secondary antibody for α2β1-integrin, demonstrated complete co-localization of these proteins in focal regions of the basal cell surface in the plane of attachment with the substratum.

Adhesion of cells to a matrix in vitro involves the transient formation of focal clusters, to which structural and signal transduction proteins are recruited, including integrins, vinculin, paxillin, and pp$^{125FAK}$(Clark and Brugge, 1995, *Science* 268:233–239). In fibroblasts, classical, mature focal adhesions are typically needle-shaped in appearance. In epithelial cells, however, larger, more globular structures have reported to form, particularly in the initial stages of adhesion to a substratum (Jockusch et al., 1995, *Rev Cell Dev Biol* 11:379–416). Double labeling immunofluorescence studies showed completely overlapping co-localization of polycystin-1 with vinculin (FIGS. 8D–F) and paxillin (FIGS. 8G–I) which were detected together with α2β1-integrin in large focal clusters at the cell membrane at points of contact with the matrix. Similarly, co-localizations of polycystin-1, α2β1-integrin, vinculin and paxillin were demonstrated in focal clusters in cultures of normal human fetal collecting tubules after short periods of adhesion to type I collagen (FIG. 9). In summary, these co-localization studies establish identical distributions of PKD-1 with α2β1-integrin, vinculin and paxillin within cluster-like structures at the cell-matrix interface in response to initial adherence to type I collagen matrix apparently both in normal and ADPKD epithelia. It should be noted, however, that, consistent with the findings presented in FIG. 5, many more ADPKD epithelia were adherent and showed cluster formation after 4 hours than fetal collecting tubule epithelia.

To establish whether there was direct physical association between PKD-1 and these co-distributing proteins, cell extracts were immunoprecipitated with anti-polycystin-1 antibodies and associated proteins examined by immunodetection using Western blotting (FIG. 10). In normal fetal collecting tubule epithelia (FIG. 10B), co-immunoprecipitation of PKD-1 with vinculin (lane 2), paxillin (lane 3) and pp125$^{FAK}$ (lane 4) was demonstrated. Interestingly, in ADPKD epithelia (FIG. 10C), although vinculin (lane 2) and paxillin (lane 3) were present in the co-Immunoprecipitates with PKD-1, pp125$^{FAK}$ (lane 4) was not apparently associated with polycystin-1 protein complexes. This therefore suggested an alteration in tyrosine phosphorylation of polycystin-1 might play a role in alterations of adhesion in ADPKD epithelia.

6.2.4 Tyrosine Phosphorylation of Polycystin-1

The deduced amino acid sequence of polycystin-1 suggests a potential site for tyrosine phosphorylation at $Tyr_{4127}$ in the cytoplasmic C-terminal domain of the protein (International PKD Consortium, 1995, *Cell* 81:289–298). To determine biochemically, whether polycystin-1 is indeed a target of tyrosine phosphorylation, two types of experiment were carried out. In the first set, parallel samples of cells were subjected to immunoblot analyses using anti-phosphotyrosine and anti-polycystin-1 (C-terminal domain) antibodies (FIGS. 11A, B). Using actively proliferating, adherent human renal epithelial primary and immortalized cell lines with detectable levels of polycystin-1 by Western blot analysis (FIG. 9A), it was shown by parallel analysis of anti-phosphytyrosine immunoreactivity on stripped blots, that polycystin-1 was tyrosine phosphorylated (FIG. 11B). As predicted, additional proteins in addition to polycystin-1 were also tyrosine phosphorylated as represented by lower molecular weight bands. The same results were obtained if anti-PKD1 blots were stripped and reprobed with anti-phosphotyrosine antibodies.

Definitive evidence that polycystin-1 can be phosphorylated on tyrosine residues was obtained by immunoprecipitation of ADPKD and normal renal epithelial cell proteins with anti-phosphotyrosine antibodies followed by immunoblot analysis with anti-polycystin-1 antibody. A major band of >440 kDa was detected in proliferative and adherent normal and ADPKD cells, indicating the tyrosine phosphorylation of polycystin-1 in these cells (FIG. 11C). Recently we have extended these findings by demonstration of tyrosine phosphorylation of the PKD-1-C-terminal domain fusion protein in vitro (L1 et al., 1999, *Am J Physiol* 263:F697–F704). Of interest, the level of tyrosine phosphorylation in the ADPKD epithelial cells appeared to be lower than in normal cells (FIG. 11C lane 1) suggesting that reduction in polycystin-1 tyrosine phosphorylation may be an important consequence of PKD1 gene mutation(s). This is consistent with the majority of mutations reported to date being deletions; missense or introduction of premature stop codons which would result in a truncated protein and removal of several putative tyrosine phosphorylation sites. It has recently shown that the phosphorylation of the PKD1-C-terminal domain fusion protein in vitro by c-src can be abrogated entirely by site directed mutation at tyrosine position Y 4237 (L1 et al., 1999, *Am J Physiol* 263: F697–F704).

Various publications are cited herein which are hereby incorporated, by reference, in their entireties.

The present invention is not to be limited in scope by the embodiments disclosed in the examples which are intended as an illustration of one aspect of the invention, and any compositions or methods which are functionally equivalent are within the scope of this invention. Indeed, various modifications of the invention in addition to those shown and described herein will become apparent to those skilled in the art from the foregoing description. Such modifications are intended to fall within the scope of the claims.

---

---

What is claimed:

1. A method for identifying a compound capable of modulating a polycystin-1 mediated increase in cell adherence to type I collagen coated substrate, comprising;
   (a) contacting a test compound with a cell expressing a polycystin-1 protein wherein expression of said polycystin-1 protein results in an increase in cell adherence to type I collagen coated substrate;
   (b) measuring cell adherence to type I collagen coated substrate; and
   (c) comparing the level of cell adherence to type I collagen coated substrate obtained in (b) to the level of cell adherence to type I collagen coated substrate obtained in the presence of a vehicle control:
   wherein a decrease in the level of cell adherence to type I collagen coated substrate obtained in (b) compared to that obtained in the presence of a vehicle control, indicates identification of a compound capable of modulating polycystin-1 activity.

2. The method of claim 1 wherein the cell is recombinantly engineered to express a mutant polycystin-1 protein.

3. The method of claim 1 wherein the polycystin-1 protein is overexpressed wherein over expression of the polycystin-1 protein results in an increase in cell adherence to type I collagen coated substrate.

4. A method for identifying a compound capable of modulating a polycystin-1 mediated increase in apical expression of NaK-ATPase on the cell membrane, comprising;
   (a) contacting a test compound with a cell expressing a polycystin-1 protein wherein expression of said polycystin-1 protein results in an increase in apical expression of NaK-ATPase on the cell membrane;
   (b) measuring apical expression of NaK-ATPase on the cell membrane; and (c) comparing the level of apical expression of NaK-ATPase on the cell membrane obtained in (b) to the level of apical expression of NaK-ATPase on the cell membrane obtained in the presence of a vehicle control:

wherein a decrease in the level of apical expression of NaK-ATPase on the cell membrane obtained in (b) compared to the level obtained in the presence of a vehicle control, indicates identification of a compound capable of modulating polycystin-1 activity.

5. The method of claim 4 wherein the cell is recombinantly engineered to express a mutant polycystin-1 protein.

6. The method of claim 4 wherein the polycystin-1 protein is expressed to a higher level as compared to endogenous polycystin-1 protein.

7. A method for identifying a compound capable of modulating a polycystin-1 mediated increased expression of β-2-NaKATPase within the cell, comprising;
(a) contacting a test compound with a cell expressing a polycystin-1 protein wherein expression of said polycystin-1 protein results in an increased expression of β-2-NaKATPase within the cell;
(b) measuring expression of β-2-NaKATPase within the cell; and
(c) comparing the level of expression of β-2-NaKATPase within the cell obtained in (b) to the level of expression of β-2-NaKATPase within the cell obtained in the presence of a vehicle control:
wherein a decrease in the level of expression of β-2-NaKATPase within the cell obtained in (b) as compared to that obtained in the presence of a vehicle control, indicates identification of a compound capable of modulating polycystin-1.

8. The method of claim 7 wherein the cell is recombinantly engineered to express a mutant polycystin-1 protein.

9. The method of claim 7 or 8 wherein the polycystin-1 protein is over expressed wherein overexpression of the polycystin-1 protein results in increased expression of β-2-NaKATPase within the cell.

10. The method of claim 7 or 8 wherein the expression of β-2-NaK-ATPase within the cell is measured using an anti-β-2-NaK-ATPase antibody.

11. A method for identifying a compound capable of modulating a polycystin-1 mediated decreased incorporation of focal adhesion kinase into focal adhesion complexes, comprising;
(a) contacting a test compound with a cell expressing a polycystin-1 protein wherein expression of said polycystin-1 protein results in a decreased incorporation of focal adhesion kinase into focal adhesion complexes;
(b) measuring incorporation of focal adhesion kinase into focal adhesion complexes; and
(c) comparing the level of incorporation of focal adhesion kinase into focal adhesion complexes obtained in (b) to the level of incorporation of focal adhesion kinase into focal adhesion complexes obtained in the presence of a vehicle control:
wherein an increase in the level of incorporation of focal adhesion kinase into focal adhesion complexes obtained in (b) as compared to that obtained in the presence of a vehicle control, indicates identification of a compound capable of modulating polycystin-1 activity.

12. The method of claim 11 wherein the cell is recombinantly engineered to express a mutant polycystin-1 protein.

13. The method of claim 12 wherein the polycystin-1 protein is over expressed wherein overexpression of the polycystin-1 protein results in decreased incorporation of focal adhesion kinase into focal adhesion complexes.

14. The method of claim 11, 12, or 13 wherein the incorporation of focal adhesion kinase into focal adhesion complexes is measured using an anti-focal adhesion kinase antibody.

15. The method of claim 11 wherein the cell expressing the polycystin-1 protein further comprises an epitope tagged focal adhesion kinase protein.

16. The method of claim 2, 5, 8 or 12 wherein the recombinantly engineered cell comprises an epitope tagged polycystin-1 interacting protein.

17. The method of claim 2, 5, 8 or 12 wherein the polycystin-1 protein is epitope tagged.

* * * * *

UNITED STATES PATENT AND TRADEMARK OFFICE
CERTIFICATE OF CORRECTION

| | |
|---|---|
| PATENT NO. | : 7,045,303 B1 |
| APPLICATION NO. | : 09/478737 |
| DATED | : May 16, 2006 |
| INVENTOR(S) | : Patricia D. Wilson and Christopher R. Burrow |

It is certified that error appears in the above-identified patent and that said Letters Patent is hereby corrected as shown below:

IN THE SPECIFICATION:

Please insert, before Col. 1, line 5 ("INTRODUCTION"), the following paragraph:

-- This invention was made with government support under NIH grant number DK44833 awarded by the National Institutes of Health. The United States Government has certain rights in the invention. --

Signed and Sealed this

Fifteenth Day of December, 2009

David J. Kappos
*Director of the United States Patent and Trademark Office*